(12) United States Patent
Kemp et al.

(10) Patent No.: US 11,141,063 B2
(45) Date of Patent: Oct. 12, 2021

(54) INTEGRATED SYSTEM ARCHITECTURES AND METHODS OF USE

(75) Inventors: Nathaniel J. Kemp, Concord, MA (US); Timothy K. Glynn, San Marcos, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 12/978,344

(22) Filed: Dec. 23, 2010

(65) Prior Publication Data

US 2012/0165661 A1 Jun. 28, 2012

(51) Int. Cl.
| | |
|---|---|
| *A61B 5/00* | (2006.01) |
| *A61B 1/00* | (2006.01) |
| *G16H 40/67* | (2018.01) |
| *G06F 19/00* | (2018.01) |

(52) U.S. Cl.
CPC ........ *A61B 5/0066* (2013.01); *A61B 1/00013* (2013.01); *A61B 1/00016* (2013.01); *A61B 1/00018* (2013.01); *A61B 5/002* (2013.01); *A61B 5/0022* (2013.01); *A61B 5/0059* (2013.01); *A61B 5/0084* (2013.01); *G06F 19/00* (2013.01); *G16H 40/67* (2018.01); *A61B 5/7232* (2013.01)

(58) Field of Classification Search
USPC ........................................ 600/407, 473, 476
See application file for complete search history.

(56) References Cited

U.S. PATENT DOCUMENTS

| | | |
|---|---|---|
| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |

(Continued)

FOREIGN PATENT DOCUMENTS

| | | |
|---|---|---|
| EP | 1041373 A2 | 10/2000 |
| EP | 01172637 A1 | 1/2002 |

(Continued)

OTHER PUBLICATIONS

Sihan et al., 2008, A novel approach to quantitative analysis of intraluminal optical coherence tomography imaging, Comput. Cardiol:1089-1092.

(Continued)

*Primary Examiner* — Oommen Jacob
*Assistant Examiner* — Shahdeep Mohammed

(57) ABSTRACT

Provided herein are systems, methods and apparatuses for an integrated system and architectures comprising a central processing unit (CPU) located a substantial physical distance from a sample.

12 Claims, 16 Drawing Sheets

(56) References Cited

U.S. PATENT DOCUMENTS

| | | |
|---|---|---|
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,195,519 A * | 3/1993 | Angelsen ............... A61B 5/416 600/454 |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,361,768 A * | 11/1994 | Webler ..................... A61B 8/12 128/916 |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A * | 10/1998 | Alekseev et al. ............. 600/477 |
| 5,820,594 A | 10/1998 | Fontirroche et al. |
| 5,824,520 A | 10/1998 | Mulligan-Kehoe |
| 5,827,313 A * | 10/1998 | Ream ........................... 606/171 |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |

(56) References Cited

U.S. PATENT DOCUMENTS

| | | | |
|---|---|---|---|
| 5,877,802 A | 3/1999 | Takahashi et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,088,144 A * | 7/2000 | Doerr ................... H04B 10/077 398/1 |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |

(56) References Cited

U.S. PATENT DOCUMENTS

| | | |
|---|---|---|
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |

(56) References Cited

U.S. PATENT DOCUMENTS

| | | |
|---|---|---|
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp, II et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0083563 A1* | 5/2003 | Katsman ............... G16H 30/20 600/407 |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0120134 A1* | 6/2003 | Rao ...................... G06Q 10/10 600/300 |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0021922 A1* | 2/2004 | Chen et al. ................ 359/212 |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |

(56) References Cited

U.S. PATENT DOCUMENTS

| | | |
|---|---|---|
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1* | 1/2007 | Donaldson .............. 600/437 |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049808 A1* | 3/2007 | Roessler .............. A61B 5/0059 600/315 |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0070194 A1 | 3/2007 | Abe |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1* | 10/2007 | Gille .............. A61B 8/467 600/481 |
| 2007/0234219 A1* | 10/2007 | Bhattaru .............. 715/744 |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |

(56) References Cited

U.S. PATENT DOCUMENTS

| | | |
|---|---|---|
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0249401 A1* | 10/2008 | Watanabe ............ A61B 8/13 600/437 |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043156 A1* | 2/2009 | Igarashi ............... A61B 1/05 600/109 |
| 2009/0043191 A1 | 2/2009 | Castella et al. |
| 2009/0046295 A1* | 2/2009 | Kemp et al. ............... 356/479 |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0087759 A1 | 4/2009 | Matsumoto |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1* | 10/2009 | Courtney et al. ............. 600/463 |
| 2009/0269014 A1 | 10/2009 | Winberg et al. |
| 2009/0270695 A1 | 10/2009 | McEowen |
| 2009/0276515 A1 | 11/2009 | Thomas et al. |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0290768 A1* | 11/2009 | De La Torre-Bueno ................... G06F 19/324 382/128 |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152578 A1* | 6/2010 | Hall ..................... A61B 8/467 600/437 |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0198081 A1 | 8/2010 | Hanlin |
| 2010/0220334 A1 | 9/2010 | Condit et al. |
| 2010/0226607 A1 | 9/2010 | Zhang et al. |
| 2010/0234736 A1* | 9/2010 | Corl ................... G10K 11/355 600/463 |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0130658 A1* | 6/2011 | Iddan ................. A61B 8/4488 600/437 |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1* | 1/2012 | Kemp ................. A61B 5/6852 600/410 |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |

(56) References Cited

U.S. PATENT DOCUMENTS

| | | |
|---|---|---|
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0226167 A1* | 9/2012 | Zuluaga ............ A61B 5/0071 600/478 |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 1075440 A | 3/1998 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003/527184 B | 9/2003 |
| JP | 2003-287534 A | 10/2003 |
| JP | 2004-500211 A | 1/2004 |
| JP | 2004/290548 A | 10/2004 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2008/504922 A | 2/2008 |
| JP | 2008-145375 A | 6/2008 |
| JP | 2008145150 A | 6/2008 |
| JP | 2009-233001 A | 10/2009 |
| JP | 2010-035690 A | 2/2010 |
| JP | 2010-042182 A | 2/2010 |
| JP | 2010-227159 A | 10/2010 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/044296 A1 | 8/2000 |
| WO | 01/11409 A2 | 2/2001 |
| WO | 01/70100 A2 | 9/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/003650 A2 | 1/2006 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |

(56) References Cited

FOREIGN PATENT DOCUMENTS

| | | | |
|---|---|---|---|
| WO | 2007/045690 A1 | 4/2007 | |
| WO | 2007/058895 A2 | 5/2007 | |
| WO | 2007/067323 A2 | 6/2007 | |
| WO | 2007/084995 A2 | 7/2007 | |
| WO | 2008/058084 A2 | 5/2008 | |
| WO | 2008/069991 A1 | 6/2008 | |
| WO | 2008086613 A1 | 7/2008 | |
| WO | 2008/107905 A2 | 9/2008 | |
| WO | 2009/009799 A1 | 1/2009 | |
| WO | 2009/009801 A1 | 1/2009 | |
| WO | 2009/046431 A1 | 4/2009 | |
| WO | 2009/087759 A1 | 7/2009 | |
| WO | 2009/121067 A1 | 10/2009 | |
| WO | 2009/137704 A1 | 11/2009 | |
| WO | 2011/06886 A2 | 1/2011 | |
| WO | 2011/038048 A1 | 3/2011 | |
| WO | 2011/081688 A1 | 7/2011 | |
| WO | 2012/003369 A2 | 1/2012 | |
| WO | 2012/061935 A1 | 5/2012 | |
| WO | 2012/071388 A2 | 5/2012 | |
| WO | 2012/087818 A1 | 6/2012 | |
| WO | 2012/098194 A1 | 7/2012 | |
| WO | 2012/109676 A1 | 8/2012 | |
| WO | 2012/130289 A1 | 10/2012 | |
| WO | 2012/154767 A2 | 11/2012 | |
| WO | 2012/155040 A1 | 11/2012 | |
| WO | 2013/033414 A1 | 3/2013 | |
| WO | 2013/033415 A2 | 3/2013 | |
| WO | 2013/033418 A1 | 3/2013 | |
| WO | 2013/033489 A1 | 3/2013 | |
| WO | 2013/033490 A1 | 3/2013 | |
| WO | 2013/033592 A1 | 3/2013 | |
| WO | 2013/126390 A1 | 8/2013 | |
| WO | 2014/109879 A1 | 7/2014 | |

OTHER PUBLICATIONS

Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelsor interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.

(56) References Cited

OTHER PUBLICATIONS

Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"—Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring—the cause of acute myocardial infarction, sudden ischaemic death, and crescendo angina, British Heart Journal 53:363-373.

Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radiofrequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).

(56) References Cited

OTHER PUBLICATIONS

International Search Report and Written Opinion dated Apr. 21, 2014, for International Patent Application No. PCT/US2013/076015, filed Dec. 18, 2013 (7 pages).
International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed on Oct. 6, 2008 (7 Pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).

Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al., 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Machine translation of JP 2000-097846, Published Apr. 7, 2000.

(56) References Cited

OTHER PUBLICATIONS

Machine translation of JP 2000-321034, Published Nov. 24, 2000.
Machine translation of JP 2000-329534, Published Nov. 30, 2000.
Machine translation of JP 2004-004080, Published Jan. 8, 2004.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome—strategies to preserve vascular access and extremity, Nephrol Dial Transplant 23:19-24.
Miller et al., 2010, The MILLER banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezam, 2008, High Speed Polygon-Scanner-Based Wavelength-Swept Laser Source in the Telescope—Less Configurations with Application in Optical Coherence Tomography, Optics Letters 33(15):1741-1743.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for In Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vase Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Machine translation of JP H11-81639.
Machine translation of JP 2000-145112.
Machine translation of JP 2004-290548.
Machine translation of JP 2007-117580.
Machine translation of JP 2008-142150.
Machine translation of JP 2010-124350.
International Search Report and Written Opinion from PCT/US2011/065465, dated Apr. 25, 2012, 18 pages.
International Search Report & Written Opinion, dated Dec. 3, 2015.

* cited by examiner

INTEGRATED SYSTEM ARCHITECTURES AND METHODS OF USE

BACKGROUND

The invention generally relates to imaging systems and more particularly to integrated architectures.

Intravascular imaging systems employ an architecture consisting of CPU components on a roll-around cart with the sample path of an interferometer extending (≈3 m) to the patient via a non-user-disconnectable Patient Interface Module (PIM) or a Patient Interface Unit (PIU) or a DOC. The short PIM cable forces the system to be located physically near the patient to avoid problems associated with long separation distance (i.e. optical dispersion and z-offset perturbation) and a permanently connected PIM cable avoids problems with connector damage/debris (i.e. insertion loss), which is difficult to avoid in the catheter lab environment when users are not trained fiber optic technicians.

Imaging systems that are integrated into surgical suites or catheterization labs have the unique challenge of transmitting information at high data rates between instrumentation which is generating interferometric signals (e.g. light source, interferometer, and photoreceivers), capturing the information (e.g. digitizer), and analyzing such information (e.g. host computer, display node, archival server, etc). Traditional imaging systems, such as that contained on a cart, do not have this challenge because the generation, capture, and analysis devices are located in close proximity and the digitizer and host are directly interconnected on a CPU's internal bus (e.g. Peripheral Component Interconnect "PCI" or Peripheral Component Interconnect express "PCIe"). Presently known devices or systems contain image capture/digitization electronics that are located in close proximity to and therefore directly coupled to the host system's bus (e.g. in a PCIe card slot). These systems do not have the challenges of transmitting high-bandwidth data across long distances (≈15+ meters).

The present invention attempts to solve these problems as well as others.

SUMMARY OF THE INVENTION

Provided herein are systems, methods and apparatuses for integrated systems. The integrated system generally comprises a control room and/or a work station that is remote from the patient table and a patient area where some portion of the integrated system resides in close proximity to the patient table allowing a user to connect an imaging device via some bedside interface. The control room and/or work station is operably associated with the patient area and the control room or work station is a substantial physical distance from the patient area.

In another embodiment, a method of integrating systems comprises: separating the computer processing unit from a sample by a substantial physical distance, wherein the substantial physical distance is at least about 5 m; operably associating an imaging system to the sample and the computer processing unit; and sending image data from the sample to the computer processing unit.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting the scope of the invention being defined by the appended claims and equivalents thereof.

Generally speaking, a variety of architecture concepts is based on an integrated system comprising a central processing unit (CPU) that is located a substantial physical distance from a sample, as shown in FIGS. 1-4. In one embodiment, the sample is a patient's vessel located within a patient area; alternatively, the sample is in any surgery suite, operation room, patient care area, operation site, and the like. The integrated systems are designed to locate the sample a substantial physical distance away from an imaging system's central processing/display/archival unit, as is necessary for cardiac catheterization lab and other procedural patient room integration including inpatient and outpatient surgical suites that are appropriate settings for the use of imaging devices (e.g. control room or remote work station separated from patient table by multiple meters). As described herein, a substantial physical distance is greater than at least 5 m, alternatively, greater than at least 10 m, alternatively, between at least 1 and 1000 m. In one embodiment, a substantial physical distance may be inside of a control room or other remote location away from the sample.

The present architectures are described herein as the imaging systems relate to Optical Coherence Tomography (OCT) systems; however, the integrated systems may also be applied to other imaging systems, including by way of example and not limitation, such as spectroscopic devices, (including fluorescence, absorption, scattering, and Raman spectroscopies), intravascular ultrasound (IVUS), Forward-Looking IVUS (FLIVUS), high intensity focused ultrasound (HIFU), radiofrequency, thermal imaging or thermography, optical light-based imaging, magnetic resonance, radiography, nuclear imaging, photoacoustic imaging, electrical impedance tomography, elastography, pressure sensing wires, intracardiac echocardiography (ICE), forward looking ICE and orthopedic, spinal imaging and neurological imaging, image guided therapeutic devices or therapeutic delivery devices, diagnostic delivery devices, and the like.

Figure 1A:
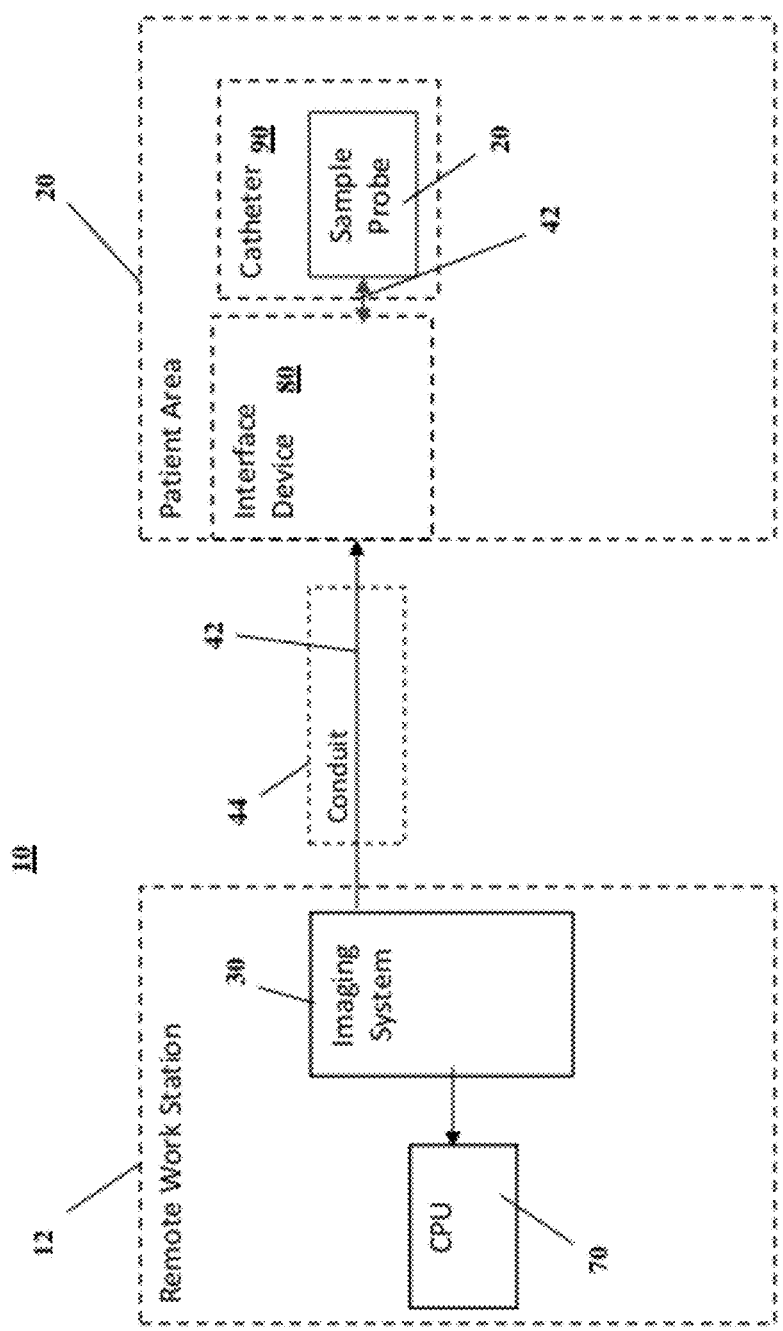
FIG. 1A is a schematic diagram of an integrated system.

In one embodiment, as shown in FIG. 1A, the integrated system 10 comprises a remote work station or control room 12 and a patient area 20, whereby the remote work station 12 is operably associated with the patient area 20 at a substantial physical distance. The remote work station 12 includes an imaging system 30 and a CPU component 70. The patient area 20 includes an interface device 80 and a catheter 90 and a sample probe 20 operably associated with the catheter 90 by way of a connection path 42. The imaging system 30 is operably associated with the patient area 20 by way of the interface device 80 through a conduit 44. The conduit 44 may include an optical fiber, electrical or wireless communication channel 42 to communicate the imaging system 30 with the interface device 80. The CPU 70 is operably associated with the imaging system 30 to enable the separation of CPU components from the sample by a substantial physical distance, as shown in FIG. 1A. In another embodiment, the integrated systems enable installation of CPU components and cables in a permanent fashion through the conduit but preserve portability and modularity of the patient interface device and catheter components, as shown in FIGS. 1-4. In another embodiment, the integrated systems enable multiple instances of the patient interface components located in various locations to interface with a single set of CPU components. The CPU components may be connected with the sample probe by way of wires, cables, optical fibers, wireless communications, and the like. Communication between any proximal and distal ends of any part of the device, system, or apparatus may be by any communication devices, such as wires, optics, wireless, RF, and the like.

In another embodiment, the integrated systems comprise an electronic subsystem that generates image data in some remote location and converts the data to digital form, as shown in FIGS. 1-4. In one embodiment, a digitizer converts the image data to digital form. This digital data is transmitted across a network and received on the opposite end of the network with another subsystem which performs other tasks (archival, analysis, display) on the data.

Generally, in an optical system for transmitting digital information, the component used to convert electrical data stream to/from the optical data stream is an optical transceiver, which is a component for high-speed optical networking. Command and control signals can also be transmitted on the network, in addition to the image data. The integrated system may include a plurality of optical transceivers and optical fibers and a plurality of wires or wireless channels can be used. High-bandwidth and long-distance image/data transmission from a remote system to a host computer uses a digital network comprising a physical layer. In one embodiment, the network's physical layer comprises an optical communication (e.g. fiber optic), an electrical communication (e.g. copper wire or coax cable for CP/IP, UDP, Firewire, USB 2, SCSI, SATA, eSATA, PCI, PCI-Express, IDE, etc.), or wireless communication (e.g. WiFi, Radiofrequency, Bluetooth, mobile communication, and the like). The digital data transfer across the network can be in serial or parallel transfer.

The term "Network" is not limited to specific consumer/commercial embodiments (such as Ethernet, USB, or Firewire), but includes any system of at least two individual members (e.g. system and host computer) that are interconnected by a communications channel in order to transmit information (e.g. image data). Image/data compression reducing transfer bandwidth can include loss compression or lossless compression. In one embodiment, the remote CPU performs decompression on a compressed incoming data stream.

Additionally, embodiments disclosed herein solve bandwidth limitations of networks by first performing image compression (e.g. JPEG or other) within the remote system before transmitting image data to the host over the network. The image compression reduces the bandwidth necessary to transmit the image data over a substantial physical distance. A remote, network-connectable system includes system front-end components (e.g. light source, interferometer, digitizer, etc) that can be kept in close proximity to the sample being imaged, versus extending the interferometer (long sample arm fiber) or source/detection path fiber optics. When the front-end system is located remotely and the transfer of information to a host computer is via a digital network transfer, a wider variety of system installation options is enabled.

Generally speaking, the method for integrating the systems with a catheter lab or other patient procedural area comprise locating the physician/patient interface components and disposables in proximity to sample; and locating the non-portable hardware a substantial physical distance away. In one embodiment, the components and disposables include the controllers, PIM, and imaging catheter. In one embodiment, the non-portable hardware includes the CPU components, power supplies, display monitors, and archival system. Generally speaking, the CPU components include power supplies, display monitors, archival system and the like, may be generally referred to as the "CPU components", and are further explained below.

The method for integrating the system further comprises connecting a patient/physician interface components with CPU components. In one embodiment, the connecting patient/physician interface includes permanently installed cables (electrical or optical) or wireless transmission. In another embodiment, the installed cables may be through a conduit, which may be a floor trench, a ceiling conduit, air for wireless transmission, and the like.

The method for integrating the systems further comprises disconnecting the patient interface components from the permanently installed components when the patient interface components are not in use, need repair, substitution, or updating. This embodiment allows for modularity, portability, serviceability, and the like of the integrated systems.

The method further comprises separating the system from its host computer and connecting with a network cable at a substantial physical distance (rather than direct host bus slot, i.e. PCI/e) to enable imaging system portability and ability to quickly interchange imaging systems and hosts (e.g. server, desktop PC, laptop PC, netbook, mobile device, etc.)

In one embodiment, the image information is transmitted from the sample to the CPU components in a manner that does not substantially reduce the quality of the image or data. Image quality reduction includes noise (e.g. electrical interference or bit errors on copper cables or wireless transmission, lossy compression), group delay dispersion (e.g. an effect in a fiber interferometer which reduces resolution and is hard to manage in long fiber cables), z-offset perturbation (mechanical or thermal changes in interferometer fiber path length), and optical insertion loss (optical transmission compromised by bent or broken fiber or dirty/damaged optical connectors). The integrated systems disclosed herein are able to fulfill these basic integration requirements to reduce noise, group delay dispersion, z-offset perturbation, and optical insertion loss.

The integrated system may be used in other medical sub-specialties outside of interventional cardiology in which an integrated OCT system is important, such as other surgical suites. The OCT applications outside of medicine could also use these integrated OCT systems for materials characterization for manufacturing, chemical identification, optical fiber architectures, and the like. Other embodiments include OCT, cardiac catheterization lab integration, OCT system architectures, Optical Frequency Domain Interferometry (OFDI), Swept-Source OCT (SS-OCT), and alternative imaging systems described above, and the like.

Generally speaking, a swept-source Fourier-domain intravascular OCT imaging system comprises: a light source and an optical interferometer. In one embodiment, the light source includes a tunable laser, a tunable-superluminescent diode (TSLED) or other tunable light source of photons. Alternatively, a light source for any other optical based imaging system may include a laser, superluminescent diode (SLD), or any other source of photons. In one embodiment, the optical interferometer includes a sample path and a reference path. A "path" may be physically co-located in the same spatial location or fiber (e.g. "common path") and can consist of a number of interferometer layouts (Michelson, Mach Zehnder, etc). Paths in the interferometer may be physically distributed over long distances and supported by fiber-optic transmission. The optical interferometer includes at least one fiber splitter/coupler or other beam-splitting/combining element for the sample and reference paths.

The OCT interferometer can be operably coupled to a sample probe. In one embodiment, the sample probe comprises a rotational catheter for intravascular imaging. In other embodiments, the sample probe includes an endoscopic probe, forward-imaging probes, galvo-scanners, or other alternative lateral scanning mechanisms for a variety of applications. The sample probe necessarily has to be located in close proximity to the sample/patient and is operably associated with the sample path of the interferometer. An exemplary sample probe is disclosed in commonly assigned U.S. patent application Ser. No. 12/172,922, incorporated by reference herein.

Additionally, the OCT interferometer is operably coupled to a photodetector or photoreceiver. The photodetector may include multiple detectors when using balanced detection and/or polarization diverse detection, e.g. splitting the sample path into separate polarization states and using at least two detectors to detect the separated polarization states. The OCT interferometer is operably coupled to a digitizer, which converts continuous analog OCT signals into sampled digital OCT signals. Analog pre-filtering and amplification are employed between the photoreceiver and digitizer.

The OCT interferometer is operably coupled with a computer or CPU component, which performs processing, display, archival, user interface, etc. functions of the system. In one embodiment, the CPU component includes multiple pieces of computing hardware distributed in different locations and interconnected with digital communication links. The CPU component can include standard PCs (desktops, laptops, servers, etc), embedded processors (Digital Signal Processors "DSP" and programmable logic arrays "PLA" such as field-programmable gate array "FPGA", etc.), graphic cards (Graphic Processing Units "GPU"), and other computing hardware/software. For an integrated imaging system, the primary computer elements are located a substantial physical distance away from the sample/patient, i.e. in the control room or remote work station. The computer can be of various types including a personal computer, a portable computer, a network computer, a control system in surgical system, a mainframe, or a remotely controlled server.

In one embodiment, the processes, systems, and methods illustrated above may be embodied in part or in whole in software that is running on a computing device or CPU components. The functionality provided for in the components and modules of the computing device may comprise one or more components and/or modules. For example, the computing device may comprise multiple central processing units (CPUs) and a mass storage device, such as may be implemented in an array of servers. Multiple CPU's and GPU's may be in a distributed fashion, as more fully described in commonly assigned U.S. patent application Ser. No. 11/868,334, incorporated by reference herein.

In general, the word "module," as used herein, refers to logic embodied in hardware or firmware, or to a collection of software instructions, possibly having entry and exit points, written in a programming language, such as, for example, Java, C or C++, or the like. A software module may be compiled and linked into an executable program, installed in a dynamic link library, or may be written in an interpreted programming language such as, for example, BASIC, Perl, Lua, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the CPU components comprises a mainframe computer suitable for controlling and/or communicating with large databases, performing high volume transaction processing, and generating reports from large databases. The CPU may comprise a conventional microprocessor. The CPU components further comprise a memory, such as random access memory ("RAM") for temporary storage of information and/or a read only memory ("ROM") for permanent storage of information, and a mass storage device, such as a hard drive, diskette, or optical media storage device. Typically, the modules of the computing system are connected to the computer using a standards based bus system. In different embodiments, the standards based bus system could be Peripheral Component Interconnect (PCI), Microchannel, SCSI, Industrial Standard Architecture (ISA) and Extended ISA (EISA) architectures, for example.

The example computing system and CPU components comprises one or more commonly available input/output (I/O) devices and interfaces, such as a keyboard, mouse, touchpad, and printer. In one embodiment, the I/O devices and interfaces comprise one or more display devices, such as a monitor, that allows the visual presentation of data to a user. More particularly, a display device provides for the presentation of GUIs, application software data, and multimedia presentations, for example. The I/O devices and interfaces also provide a communications interface to various external devices. The computing system may also comprise one or more multimedia devices, such as speakers, video cards, graphics accelerators, and microphones, for example.

In an alternative embodiment, the OCT interferometer includes a Variable Delay Line (VDL) in the either sample or reference path. The VDL is used to compensate for small pathlength variations in the interferometer during system use. The integrated OCT system may also include a Patient Interface Module (PIM), which is used in intravascular OCT systems for interfacing a rotational catheter with rotation and translation drive motors. Alternatively, PIM's may be any interface module to couple an imaging system component to the catheter, sample, or sample probe. The PIM component as designated can consist of either a single physical box or multiple separate boxes (separated with cables, wireless connections, and the like). For example, one interface module has the light source, detectors, digitizer, reference arm in the PIM box and the motor and catheter interface in a separate PIM box. Alternatively, the interface module may be a longitudinal pullback device, such as the Volcano™ Revolution™ PIM, the Volcano™ R100, or the Volcano™ Trak Back II Catheter Pull-Back Device, for operation of a rotational catheter or other imaging catheter.

In an alternative embodiment, the OCT interferometer includes a Sample Clock Generator. Light sources with non-linear sweep profiles must be accompanied by a sample clock generator which effectively synchronizes the light source output to the digitizer via a separate clocking interferometer (e.g. "wavemeter") and photodetector subsystem. Light sources with linear (in k-space) sweeps can use a digitizer's internal (on-board) sample clock generator. The sample clock generator scheme is an important component for SS-OCT. Like other components, its location can be distributed physically over a significant distance and can share common elements with the OCT system (interferometer, detectors, digitizer, and the like). An exemplary clock generator is disclosed in commonly assigned U.S. patent application Ser. No. 12/172,980, incorporated by reference herein.

In another embodiment, the OCT interferometer may be a "fiber-based" SS-OCT system. The SS-OCT system generally comprises a Light Source and an Optical interferometer in communication with the light source by a source path. The SS-OCT system comprises a sample path operably associated with a scanning probe. The scanning probe is in communication with the rest of the interferometer via optical fiber in the sample path. The SS-OCT system comprises photodetectors in communication with the Optical interferometer through the detection path. The photodetectors are in communication with the digitizers via analog signal transmission over electrical wires, commonly including electronic analog amplification/filtering stages. The digitizers are in communication with the CPU via digital communication (electrical, digital optical, or wireless; parallel or serial data transmission; computer data bus) or analog. An exemplary SS-OCT system is described in U.S. patent application Ser. No. 12/172,980, and incorporated by reference herein.

In a "non-fiber-based" SS-OCT system, the fiber components can be replaced with bulk optical components (beamsplitters, lenses, mirrors, polarizers, etc) and the optical beams are transmitted through open space. Photodetector/Digitizer/Computer connectivity remains the same.

In a Spectral Domain (spectrometer-based) OCT system, the same components are used with a few modifications. The light source is no longer tunable, but is a broadband short-coherence length source. The photodetectors are replaced with a spectrometer and detector array and the digitizer is usually referred to as a frame grabber, although its function is basically the same. All other basic system components and interconnectivity are the same.

Other intravascular imaging systems follow the same architectural paradigm of physically containing all system elements (except for the sample path which extends to the sample via the PIM and catheter) together inside a cart or mobile console. The digitizer is usually contained within the computer and is connected via a high-speed internal data bus of the computer (e.g. PCI, PCIe). The photodetectors can be located on the same card as the digitizer, as can some embedded processing units. Many specific configurations of the basic elements are possible, but all maintain the same physical co-location in a mobile cart. The integrated system architectures disclosed herein enable a paradigm in which the primary system elements are not physically co-located in the same cart or mobile console.

Figure 1B:
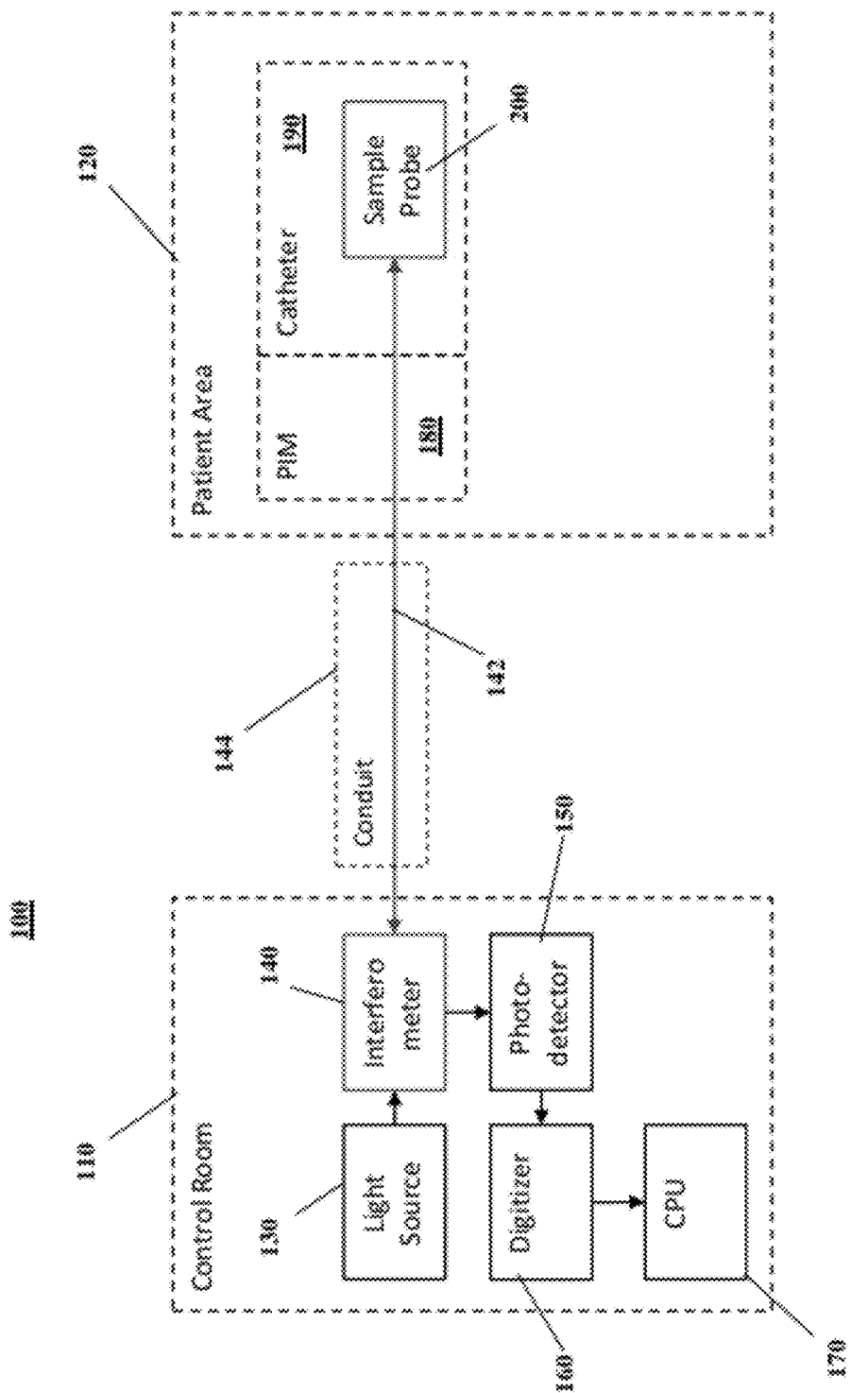
FIG. 1B is a schematic diagram of an extended interferometer sample path.

In one embodiment, the integrated OCT system 100 is shown in FIG. 1B, which is an extended interferometer sample path. The integrated OCT system 100 comprises a control room or a remote work station 110 and a patient area 120, whereby the remote work station 110 is operably associated with the patient area 120. The control room 110 may be any general area or location that is a substantial physical distance from the patient area 120, such as the remote work station. The control room 110 comprises a light source 130 operably associated with an interferometer 140, a photodetector 150 operably associated with the interferometer 140, a digitizer 160 operably associated with the photodetector 150, and a CPU 170 operably associated with the digitizer 160. The patient area 120 comprises a PIM 180 operably associated with a catheter 190, and a sample probe 200 operably associated with the catheter 190. The interferometer 140 includes an extended sample path 142 that operably associates with the sample probe 200 to integrate the control room OCT system with the Patient Area and PIM 180. Generally speaking, the extended sample path 142 is provided within a conduit 144, whereby the conduit may be an optical fiber, an electrical coupling, and the like. The integrated OCT system 100 locates the OCT sample a substantial physical distance away from the OCT system's central processing/display/archival unit. The CPU 170 in the control room 110 is for the imaging and processing of the images obtained from the catheter 190 and sample probe 200.

Figure 1C:
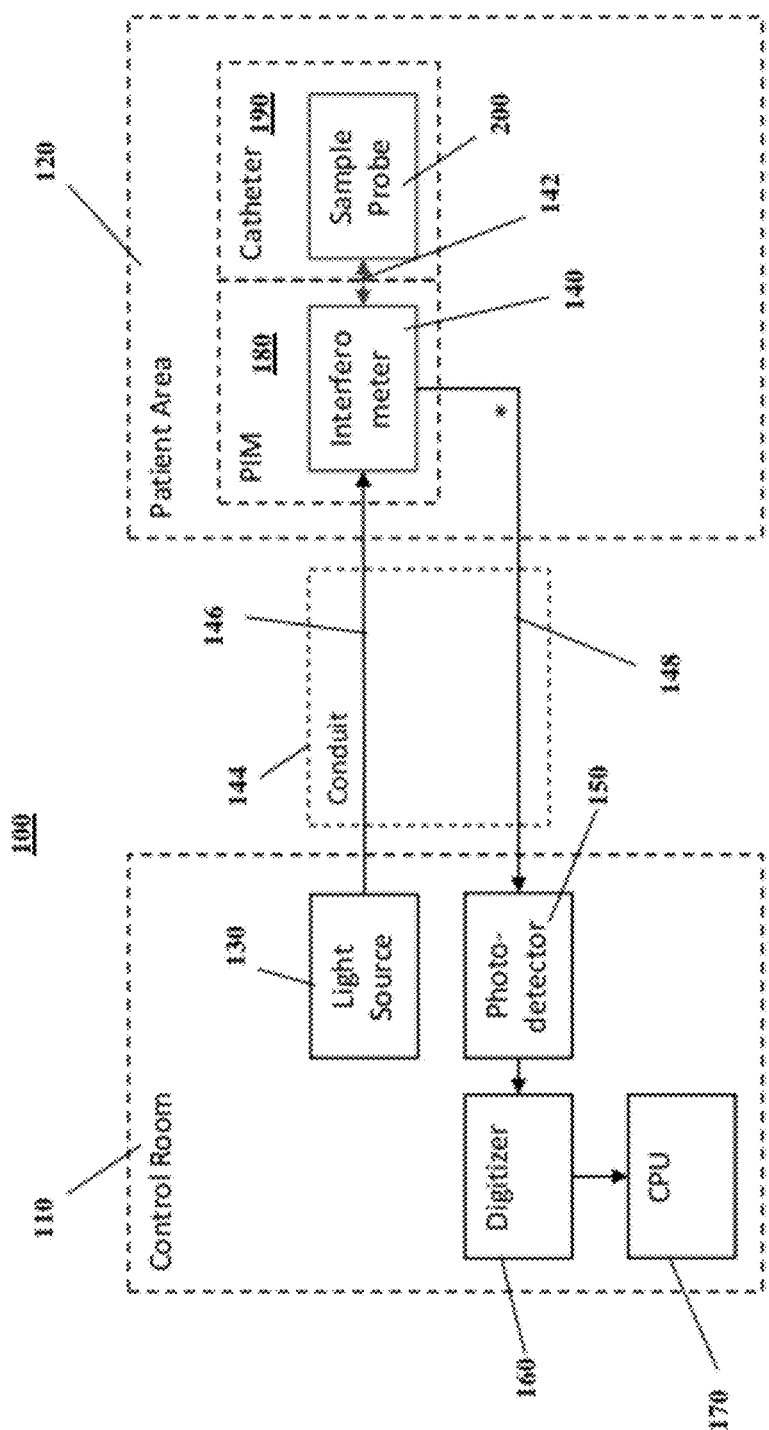
FIG. 1C is a schematic diagram of an extended source path and detector system.

In another embodiment or architecture, the integrated OCT system 100 is shown in FIG. 1C, which is an extended source path and detector system. The integrated OCT system 100 in this embodiment comprises the control room 110 and the patient area 120, whereby the control room 110 is operably associated with the patient area 120 at a substantial physical distance. The control room 110 comprises the light source 130, the photodetector 150 operably associated with the digitizer 160, and the CPU 170 operably associated with the digitizer 160. The patient area 120 comprises the PIM 180 which includes the interferometer 140 operably associated with the sample probe 200 by the sample path 142, whereby the catheter 190 includes the sample probe 200. The light source 130 is operably associated with the interferometer 140 at a substantial physical distance by a source path 146 through the conduit 144, and a detection path is operably associated with the interferometer and the photodetector 150 through the conduit 144. If a Michelson interferometer is employed then a shared source path 146 and detection path 148 are used. If a Mach-Zehnder interferometer is employed, then a separate detection path 148 from the path 146 may be used. The CPU 170 in the control room 110 is for the imaging and processing of the images obtained from the catheter 190 and sample probe 200.

Figure 2A:
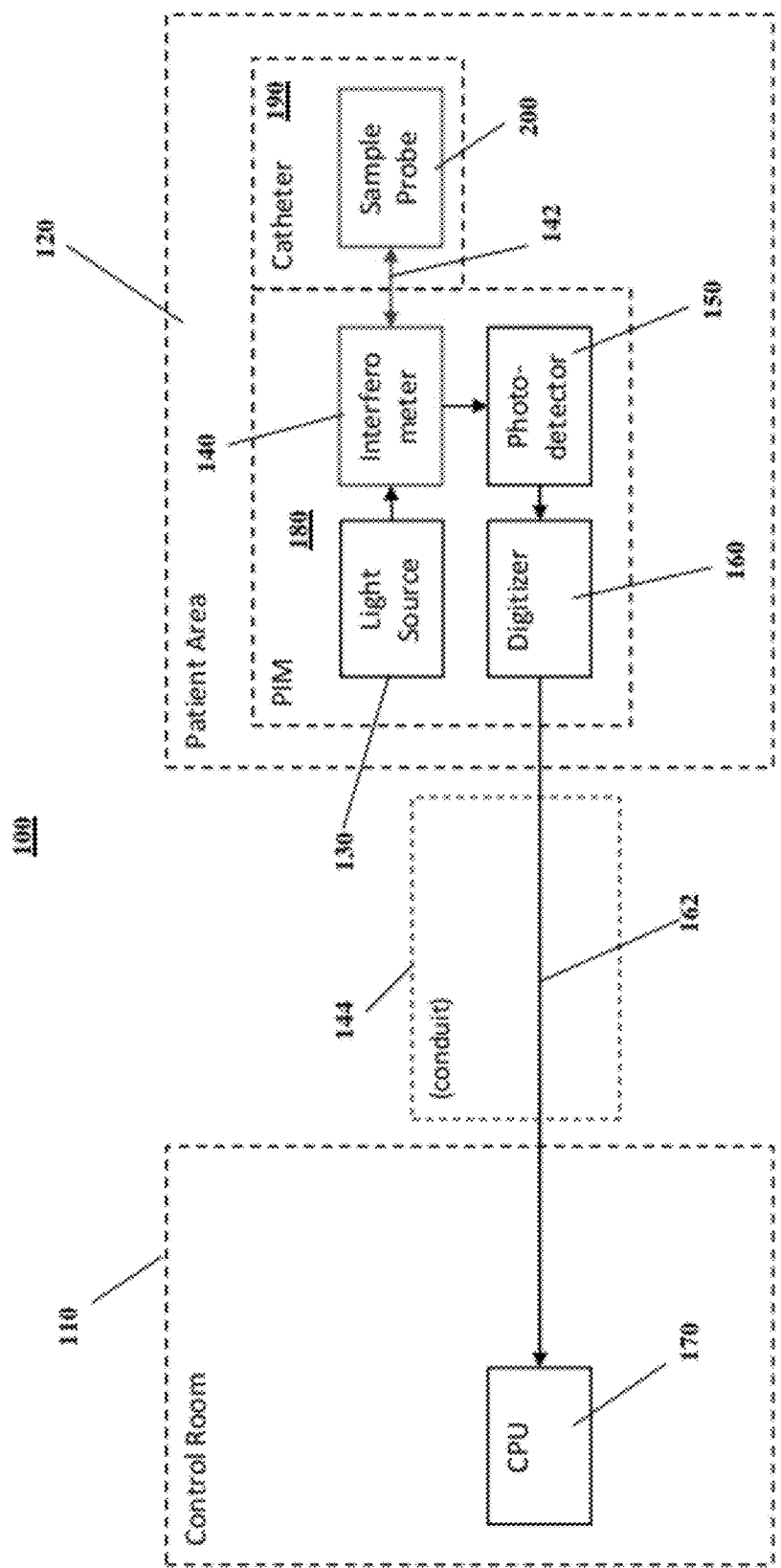
FIG. 2A is a schematic diagram of an extended digitizer-CPU system.

In another embodiment, the integrated OCT system 100 is shown in FIG. 2A, which is an extended digitizer-CPU system. The integrated OCT system 100 in this embodiment comprises the control room 110 and the patient area 120, whereby the control room 110 is operably associated with the patient area 120 at a substantial physical distance. The control room 110 comprises the CPU 170 and the patient area 120 comprises the PIM 180 and the catheter 190. The PIM 180 includes the light source 130, the interferometer 140, the photodetector 150, and the digitizer 160. The light source 130 is operably associated with the interferometer 140 within the PIM 180, while the interferometer 140 operably associated with the sample probe 200 by the sample path 142. With the interferometer 140 included in the PIM 180, the sample path 142 does not traverse a substantial physical distance, but is rather locally connected with the catheter 190. The interferometer 140 is operably associated with the photodetector 150 in the PIM 180, while the photodetector 150 is operably associated with the digitizer 160 within the PIM 180. The digitizer 160 is operably associated with the CPU 170 in the control room 170 by way of CPU path 162 that is operably associated with the conduit 144. The integrated OCT system 100 locates the OCT sample a substantial physical distance away from the OCT system's central processing/display/archival unit. The CPU 170 in the control room 110 is for the imaging and processing of the images obtained from the catheter 190 and sample probe 200.

Figure 2B:
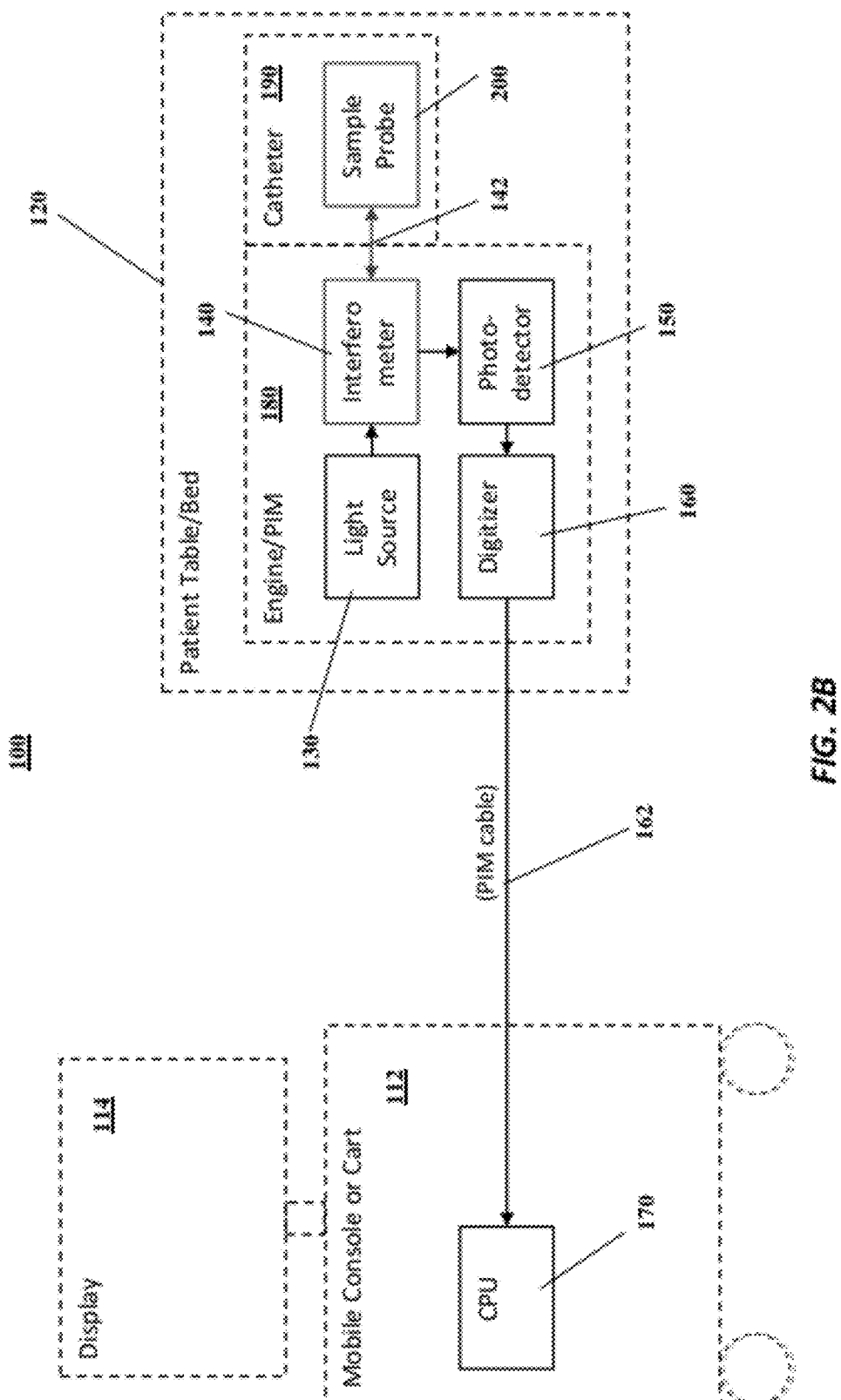
FIG. 2B is a schematic diagram of an extended digitizer-CPU mobile system.

In another embodiment, the integrated OCT system 100 is shown in FIG. 2B, which is an extended digitizer-CPU mobile system. The integrated OCT system 100 in this embodiment comprises a mobile console 112 and the patient area 120, whereby the mobile console 112 is operably associated with the patient area or patient bedside 120 at a physical distance. The mobile console 112 includes wheels or other mobile transport devices that allow the mobile console 112 to travel with the CPU 170. The mobile console 110 comprises the CPU 170 and a display 114 and the patient area 120 comprises the PIM engine 180 and the catheter 190. The PIM 180 includes the light source 130, the interferometer 140, the photodetector 150, and the digitizer 160. The light source 130 is operably associated with the interferometer 140 within the PIM 180, while the interferometer 140 operably associated with the sample probe 200 by the sample path 142. With the interferometer 140 included in the PIM 180, the sample path 142 does not traverse a substantial physical distance, but is rather locally connected with the catheter 190. The interferometer 140 is operably associated with the photodetector 150 in the PIM 180, while the photodetector 150 is operably associated with the digitizer 160 within the PIM 180. The digitizer 160 is operably associated with the CPU 170 in the mobile console 112 by way a PIM cable 162. The PIM cable 162 may be any connecting device and disconnected with the mobile console 112 through known connecting devices, female/male connectors, and the like. The CPU 170 in the control room 110 is for the imaging and processing of the images obtained from the catheter 190 and sample probe 200.

Figure 2C:
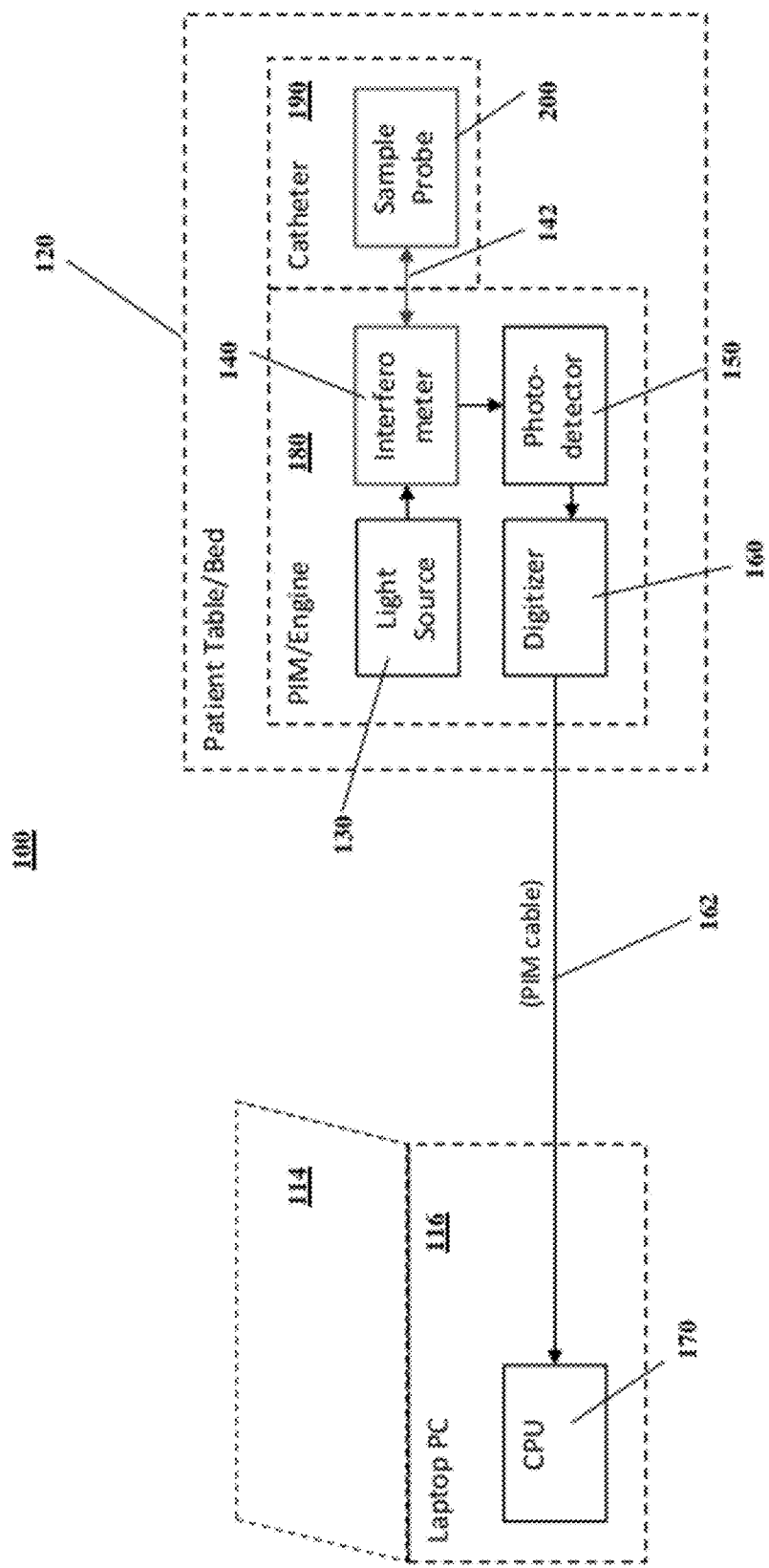
FIG. 2C is an extended digitizer-CPU laptop system.

In another embodiment, the integrated OCT system 100 is shown in FIG. 2C, which is an extended digitizer-CPU laptop system. The integrated OCT system 100 in this embodiment comprises a laptop 116 and the patient area 120, whereby the laptop 116 is operably associated with the patient area or patient bedside 120 at a physical distance. The laptop 116 includes any computer-related device with a CPU 170, including, but not limited to netbooks, tablets, PDA's, mobile phones, music players, and the like, which may travel with the CPU 170. The laptop 116 comprises the CPU 170 and a display 114 and the patient area 120 comprises the PIM engine 180 and the catheter 190. The PIM 180 includes the light source 130, the interferometer 140, the photodetector 150, and the digitizer 160. The light source 130 is operably associated with the interferometer 140 within the PIM 180, while the interferometer 140 operably associated with the sample probe 200 by the sample path 142. With the interferometer 140 included in the PIM 180, the sample path 142 does not traverse a substantial physical distance, but is rather locally connected with the catheter 190. The interferometer 140 is operably associated with the photodetector 150 in the PIM 180, while the photodetector 150 is operably associated with the digitizer 160 within the PIM 180. The digitizer 160 is operably associated with the CPU 170 in the laptop 116 by way of PIM cable 162. The PIM cable 162 may be disconnected with the laptop 116 through known connecting devices, female/male connectors, USB connectors, video cables, HDMI cables, and the like. The CPU 170 in the control room 110 is for the imaging and processing of the images obtained from the catheter 190 and sample probe 200.

Figure 3A:
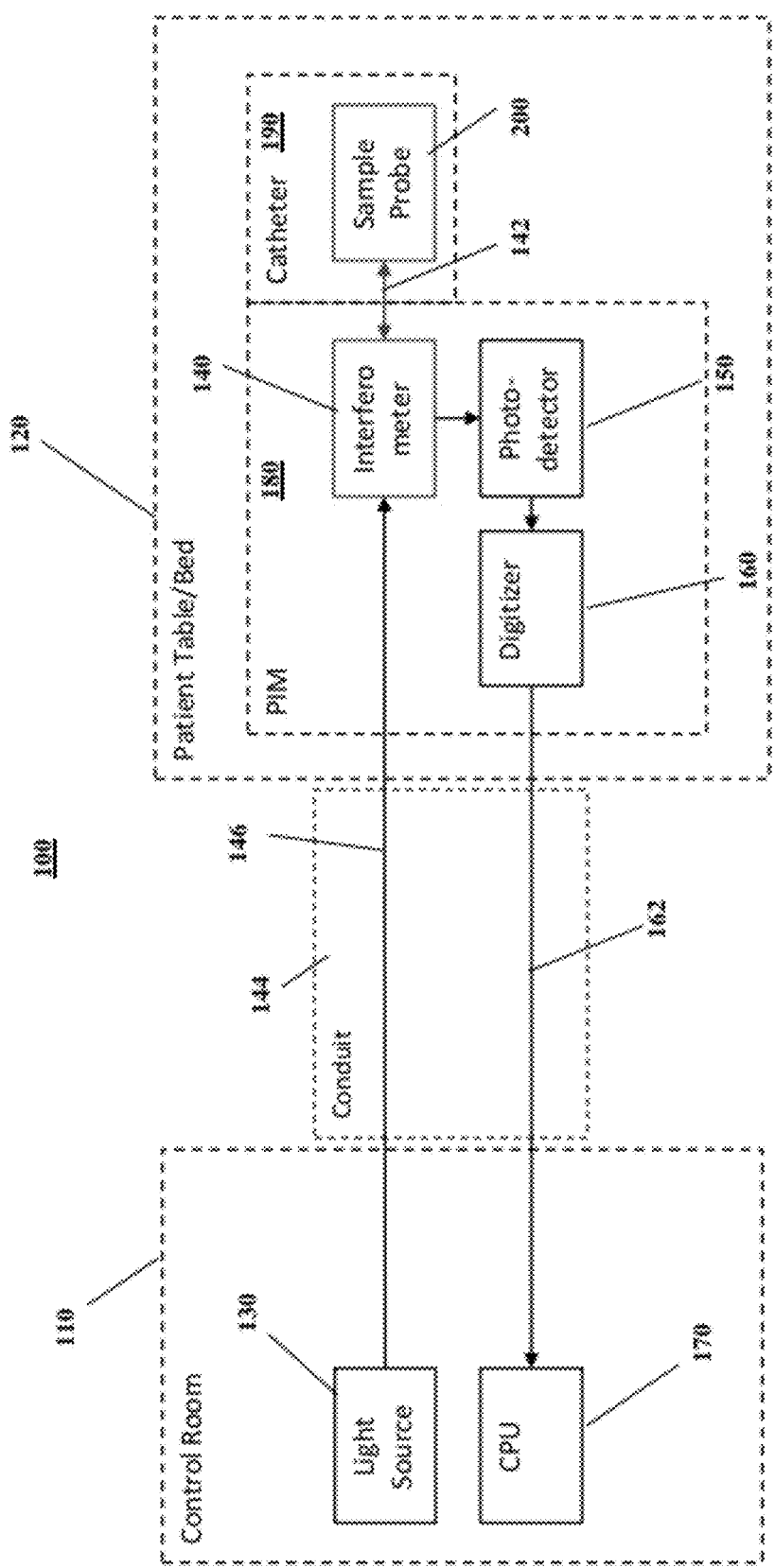
FIG. 3A is a schematic diagram of a dual light path and digital PIM cable system.

In another embodiment, the integrated OCT system 100 is shown in FIG. 3A, which is dual light path and PIM cable system. The integrated OCT system 100 in this embodiment comprises the control room 110 including the light source 130 and the CPU 170 while being operably associated with the Patient Table/Bed 120 that includes the PIM 180 and the catheter 190. The patient table 120 is located at a substantial physical distance from the control room 110. The light source 130 in the control room 110 is operably associated with the PIM 180 by way of a source path 146. The PIM 180 includes the interferometer 140, the photodetector 150, and the digitizer 160, whereby the interferometer 140 is operably associated with the source path 146. The interferometer 140 is further operably associated with the sample probe 200 by way of the sample path 142. With the interferometer 140 included in the PIM 180, the sample path 142 does not traverse a substantial physical distance, but is rather locally connected with the catheter 190 and the sample probe 200. The interferometer 140 is operably associated with the photodetector 150 in the PIM 180, while the photodetector 150 is operably associated with the digitizer 160 within the PIM 180. The digitizer 160 is operably associated with the CPU 170 in the control room 110 by way of PIM cable 162 through the conduit 144. The PIM cable 162 may be disconnected with the control room 110 through known connecting devices, female/male connectors, USB connectors, video cables, HDMI cables, and the like. The integrated OCT system 100 locates the OCT sample a substantial physical distance away from the OCT system's central processing/display/archival unit. The CPU in the control room 110 is for the imaging and processing of the images obtained from the catheter 190 and sample probe 200.

Figure 3B:
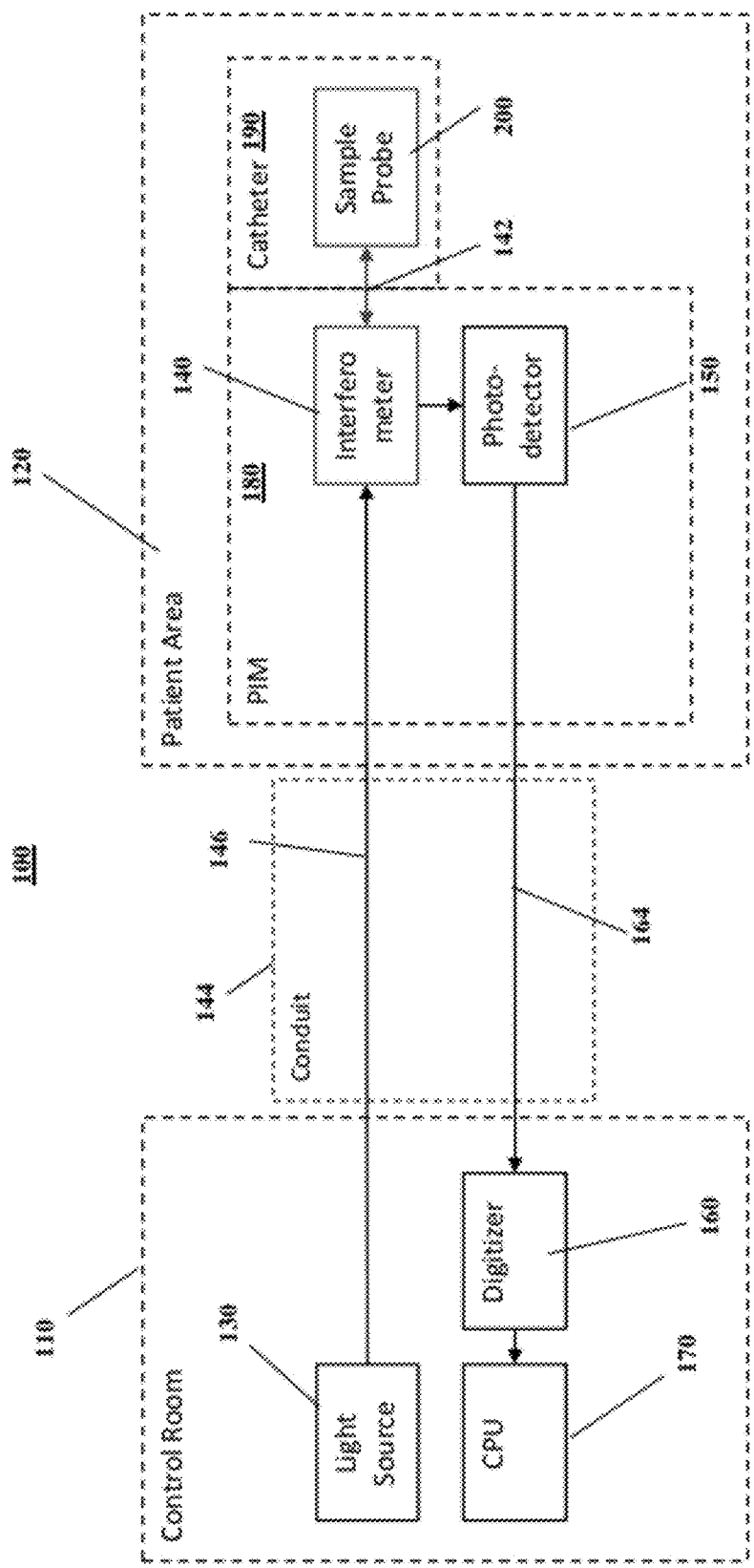
FIG. 3B is a schematic diagram of a dual light path and analog PIM cable system.

In another embodiment, the integrated OCT system 100 is shown in FIG. 3B, which is dual light path and PIM cable system. The integrated OCT system 100 in this embodiment comprises the control room 110 including the light source 130, the CPU 170, and the digitizer 160 while being operably associated with the Patient Table/Bed 120 that includes the PIM 180 and the catheter 190. The patient area 120 is located at a substantial physical distance from the control room 110. The light source 130 in the control room 110 is operably associated with the PIM 180 by way of a source path 146. The PIM 180 includes the interferometer 140 and the photodetector 150, whereby the interferometer 140 is operably associated with the source path 146. The interferometer 140 is further operably associated with the sample probe 200 by way of the sample path 142. With the interferometer 140 included in the PIM 180, the sample path 142 does not traverse a substantial physical distance, but is rather locally connected with the catheter 190 and the sample probe 200. The interferometer 140 is operably associated with the photodetector 150 in the PIM 180, while the photodetector 150 is operably associated with the digitizer 160 by way of a digitizer path 164 through the conduit 144. The digitizer 160 is operably associated with the CPU 170 in the control room 110. The digitizer path 164 may be disconnected with the control room 110 through known connecting devices, female/male connectors, USB connectors, video cables, HDMI cables, and the like. The CPU 170 in the control room 110 is for the imaging and processing of the images obtained from the catheter 190 and sample probe 200.

Figure 3C:
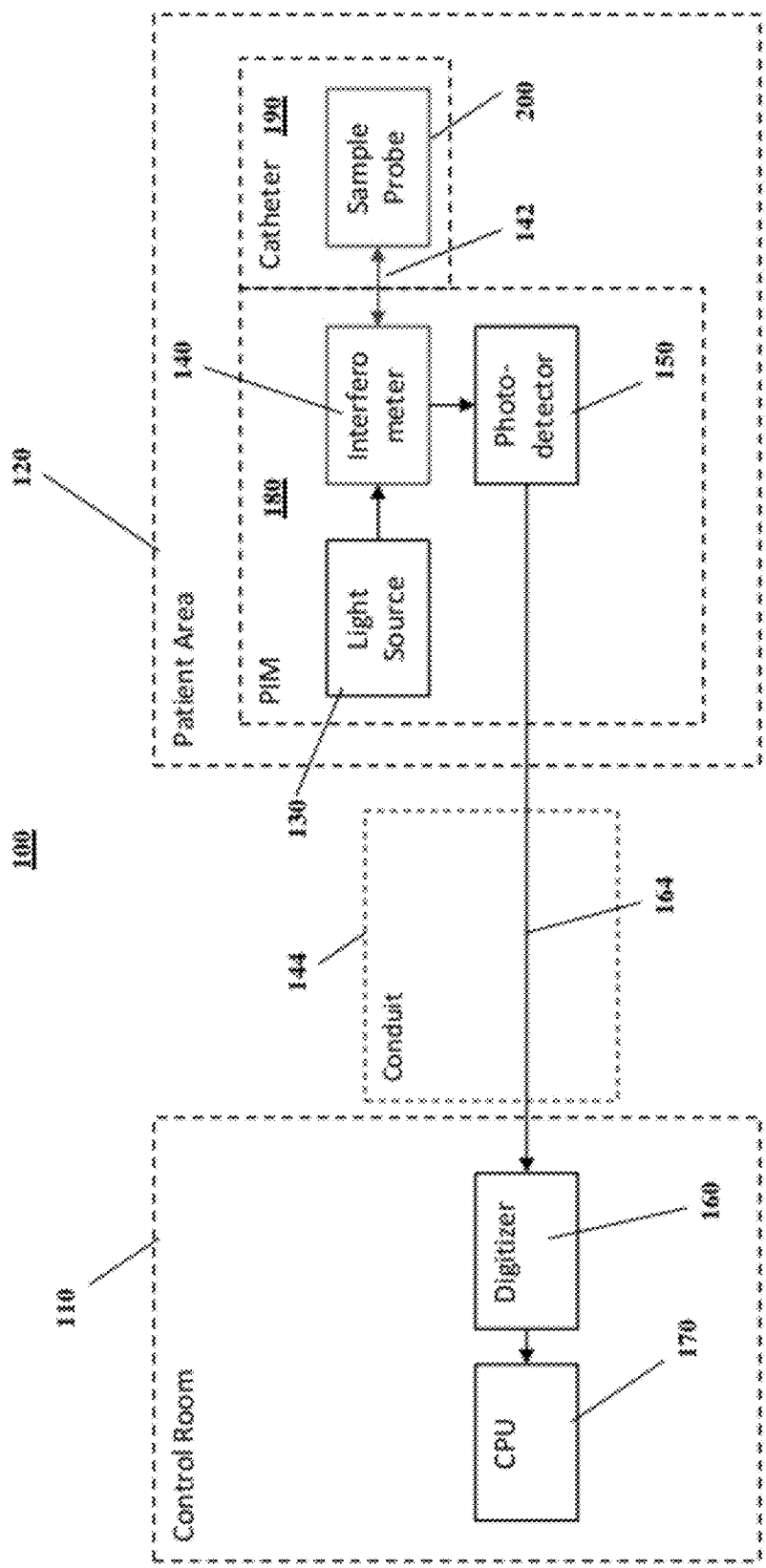
FIG. 3C is a schematic diagram of a PIM integrated interferometer system.

In another embodiment, the integrated OCT system 100 is shown in FIG. 3C, which is PIM integrated interferometer system. The integrated OCT system 100 in this embodiment comprises the control room 110 including the CPU 170 and the digitizer 160 while being operably associated with the patient area 120 that includes the PIM 180 and the catheter 190. The patient area 120 is located at a substantial physical distance from the control room 110. The PIM includes the light source 130, the interferometer 140, and the photodetector 150, whereby the interferometer 140 is operably associated with the photodetector 150 with the PIM 180. The interferometer 140 is further operably associated with the sample probe 200 by way of the sample path 142. With the interferometer 140 included in the PIM 180, the sample path 142 does not traverse a substantial physical distance, but is rather locally connected with the catheter 190 and the sample probe 200. The interferometer 140 is operably associated with the photodetector 150 in the PIM 180, while the photodetector 150 is operably associated with the digitizer 160 by way of a digitizer path 164 through the conduit 144. The digitizer 160 is operably associated with the CPU 170 in the control room 110. The digitizer path 164 may be disconnected with the control room 110 through known connecting devices, female/male connectors, USB connectors, video cables, HDMI cables, and the like. The CPU in the control room 110 is for the imaging and processing of the images obtained from the catheter 190 and sample probe 200.

Figure 3D:
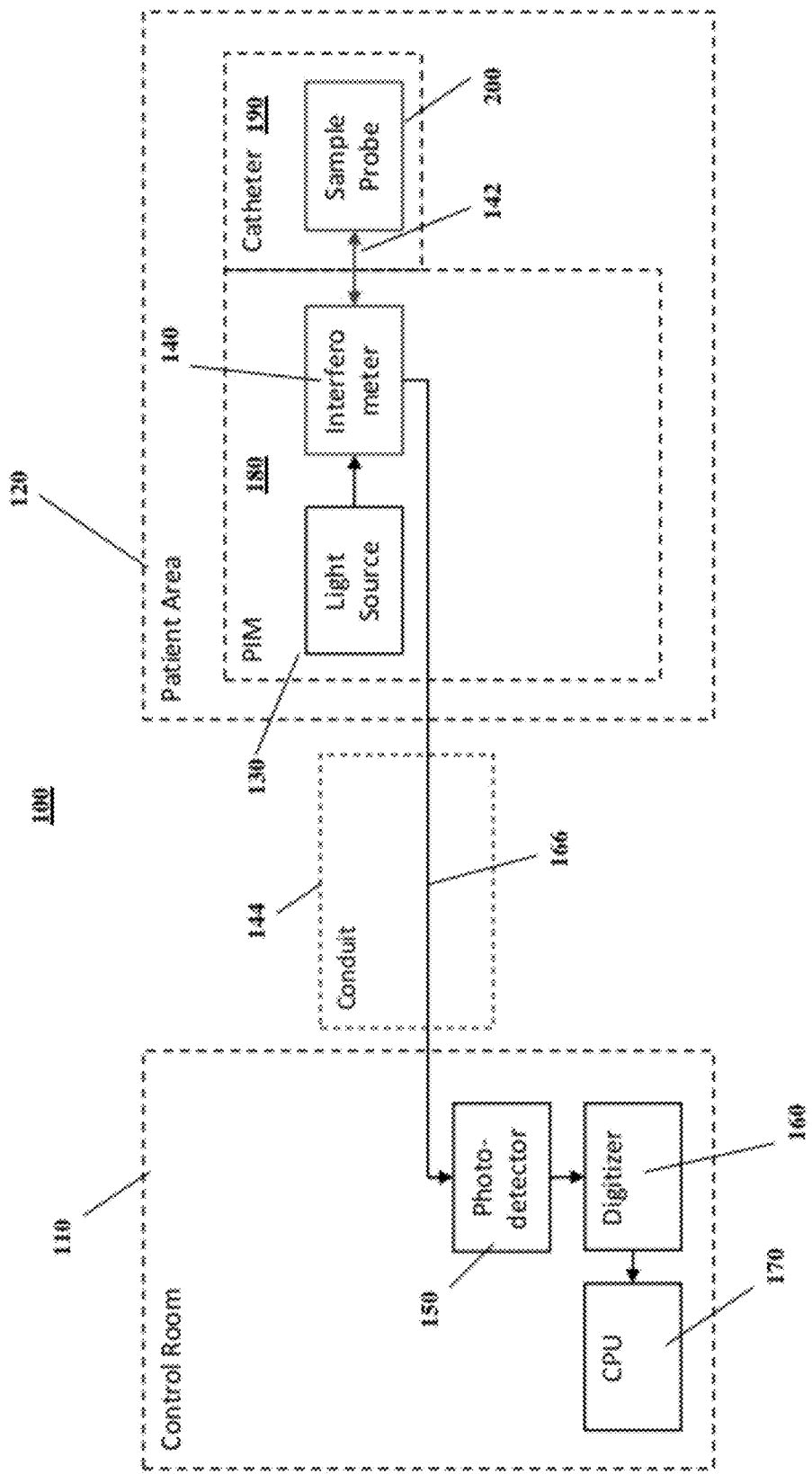
FIG. 3D is a schematic diagram of a PIM integrated interferometer system.

In another embodiment, the integrated OCT system 100 is shown in FIG. 3D, which is PIM integrated interferometer system. The integrated OCT system 100 in this embodiment comprises the control room 110 including the CPU 170, the digitizer 160, and the photodetector 150 while being operably associated with the Patient Table/Bed 120 that includes the PIM 180 and the catheter 190. The patient area 120 is located at a substantial physical distance from the control room 110. The PIM includes the light source 130 and the interferometer 140, whereby the interferometer 140 is operably associated with the photodetector 150 by way of a detection path 166. The interferometer 140 is further operably associated with the sample probe 200 by way of the sample path 142. With the interferometer 140 included in the PIM 180, the sample path 142 does not traverse a substantial physical distance, but is rather locally connected with the catheter 190 and the sample probe 200. The interferometer 140 is operably associated with the photodetector 150 by way of the detection path 166 through the conduit 144. The photodetector 150 in the control room 110 is operably associated with the digitizer 160 and the digitizer 160 is operably associated with the CPU 170 in the control room 110. The detection path 166 may be disconnected with the control room 110 through known connecting devices, female/male connectors, USB connectors, video cables, HDMI cables, and the like. The CPU in the control room 110 is for the imaging and processing of the images obtained from the catheter 190 and sample probe 200.

Figure 4A:
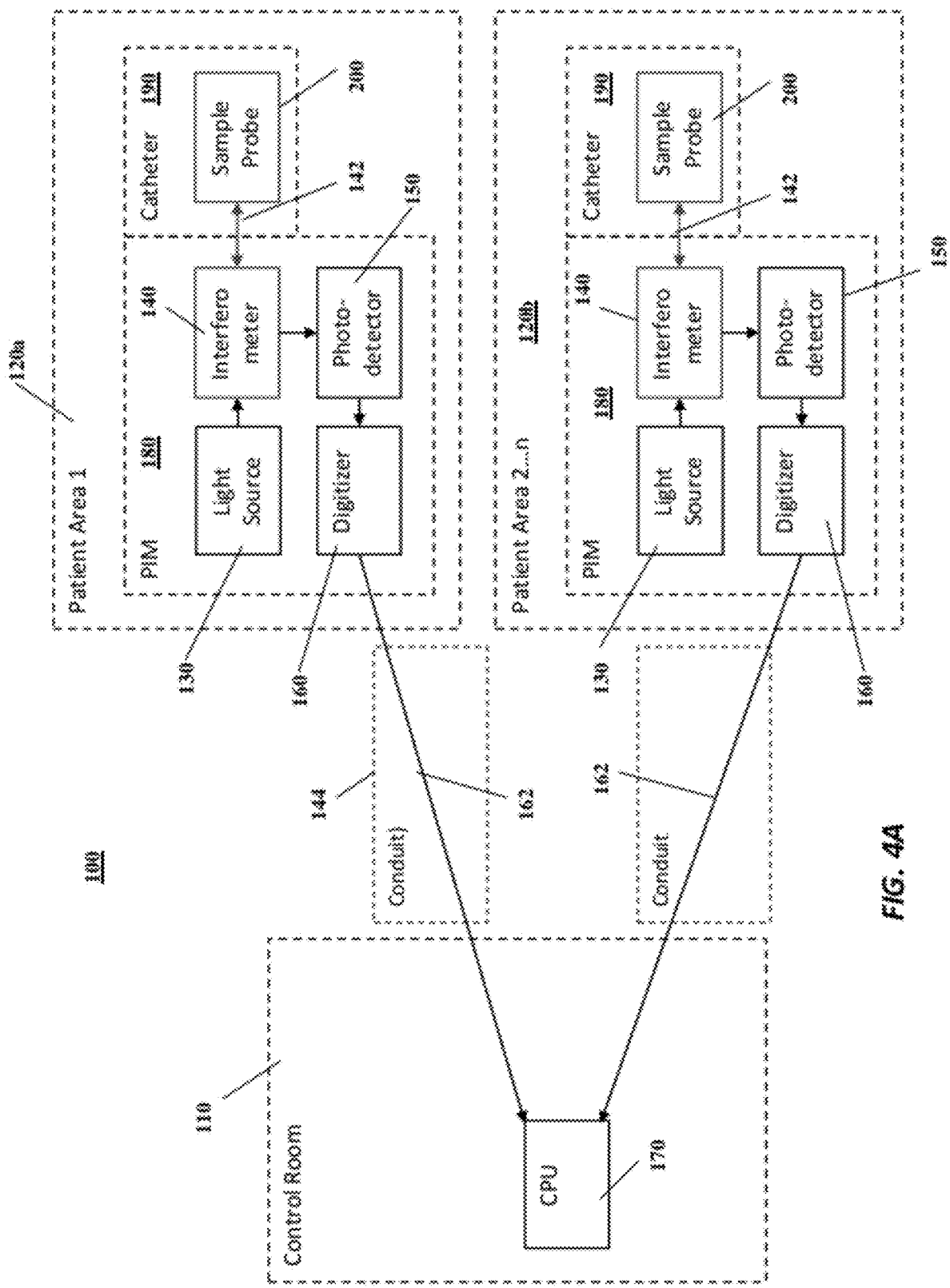
FIG. 4A is a schematic diagram of a distributed interferometer system.

In another embodiment, the integrated OCT system 100 is shown in FIG. 4A, which is a distributed interferometer system. The integrated OCT system 100 in this embodiment comprises the control room 110 including the CPU 170 operably associated with at least two patient areas 120a and 120b. The patient areas 120a and 120b effectively distribute the CPU 170 capabilities to multiple patient areas when the control room 110 is located at a substantial physical distance away from such patient areas 120a and 120b. The patient areas 120a and 120b include the PIM 180 and the catheter 190, whereby the PIM 180 includes the light source 130, the interferometer 140, the photodetector 150, and the digitizer 160. The interferometer 140 is operably associated with the sample probe 200 in the catheter 190 by the sample path 142. The digitizer 160 in the PIM 180 is operably associated with the CPU 170 in the control room 110 by way of the CPU path 162. The CPU 170 is operable with multiple inputs for the CPU paths 162, as to accept multiple CPU paths 162 from multiple PIMs 180 and patient areas 120a and 120b. The integrated OCT system 100 locates the OCT sample a substantial physical distance away from the OCT system's central processing/display/archival unit. The CPU 170 in the control room 110 is for the imaging and processing of the images obtained from the catheter 190 and sample probe 200.

Figure 4B:
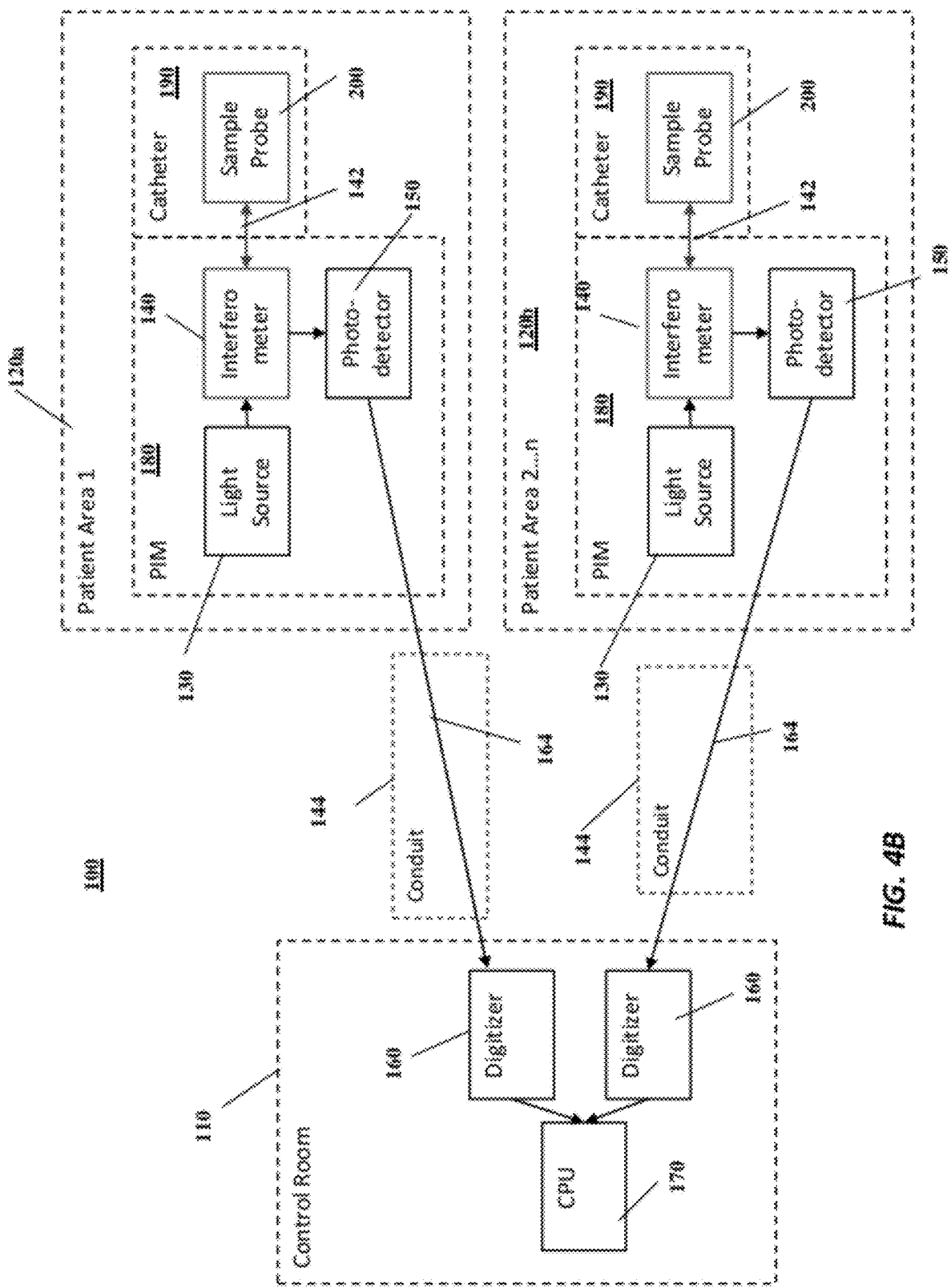
FIG. 4B is a schematic diagram of another distributed interferometer system.

In another embodiment, the integrated OCT system 100 is shown in FIG. 4B, which is another distributed interferometer system. The integrated OCT system 100 in this embodiment comprises the control room 110 including the CPU 170 and at least two digitizers 160a and 160b operably associated with at least two patient areas 120a and 120b, respectively. The patient areas 120a and 120b and the two digitizers 160a and 160b effectively distribute the CPU 170 capabilities to multiple patient areas when the control room 110 is located at a substantial physical distance away from such patient areas 120a and 120b. The patient areas 120a and 120b include the PIM 180 and the catheter 190, whereby the PIM 180 includes the light source 130, the interferometer 140, and the photodetector 150. The interferometer 140 is operably associated with the sample probe 200 in the catheter 190 by the sample path 142. The photodetector 150 is operably associated with the digitizers 160a and 160b in the control room 110 by way of the digitizer path 164. The CPU 170 is operable with multiple inputs for the digitizers 160a and 160b, as to accept multiple photodetectors 150 from multiple PIMs 180 and patient areas 120a and 120b. The CPU 170 in the control room 110 is for the imaging and processing of the images obtained from the catheter 190 and sample probe 200.

Figure 4C:
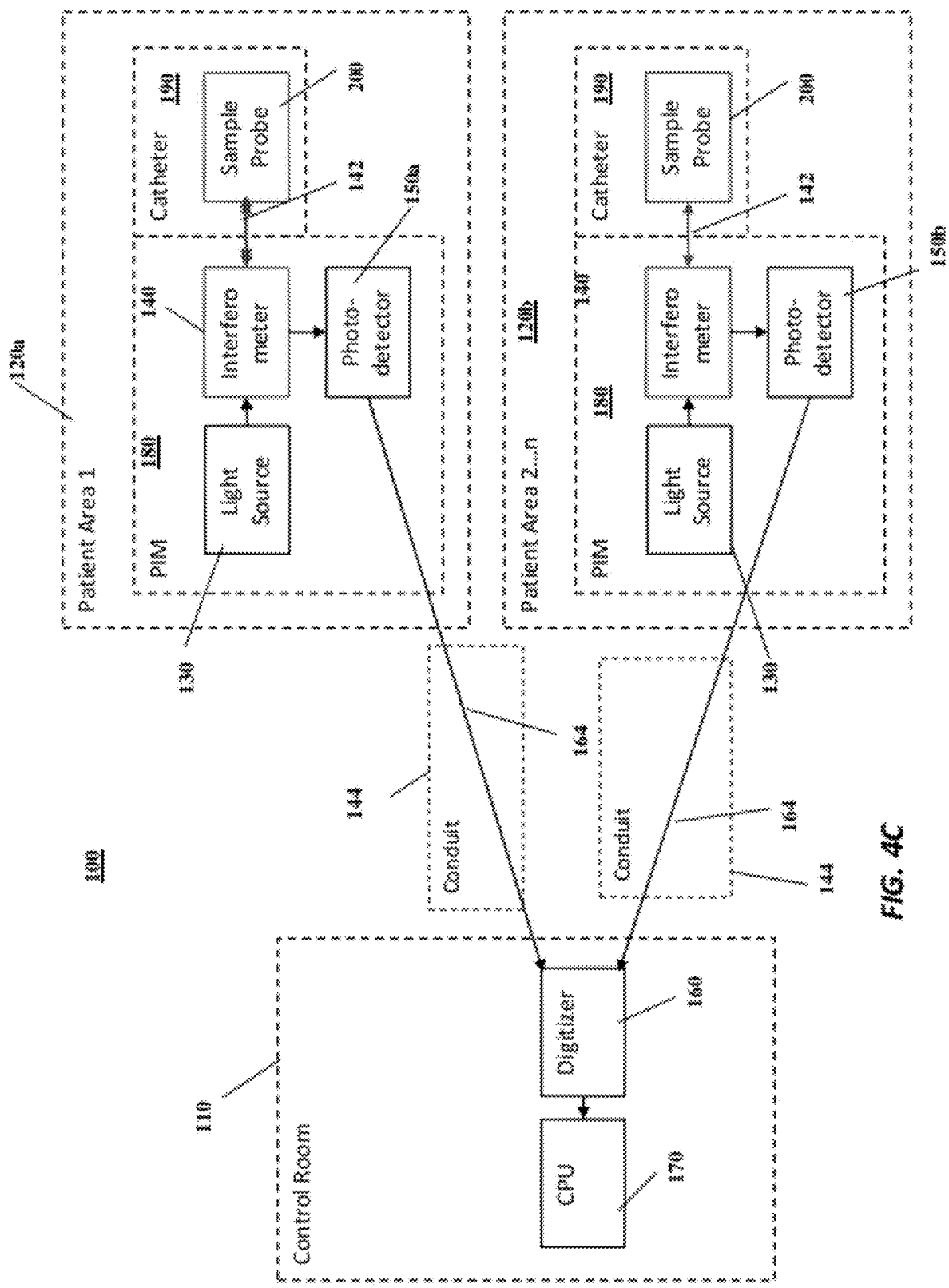
FIG. 4C is a schematic diagram of another distributed interferometer system.

In another embodiment, the integrated OCT system 100 is shown in FIG. 4C, which is another distributed interferometer system. The integrated OCT system 100 in this embodiment comprises the control room 110 including the CPU 170 and a single digitizer 160 operably associated with at least two patient areas 120a and 120b. The patient areas 120a and 120b and the digitizers 160 effectively distribute the CPU 170 capabilities to multiple patient areas when the control room 110 is located at a substantial physical distance away from such patient areas 120a and 120b. The patient areas 120a and 120b include the PIM 180 and the catheter 190, whereby the PIM 180 includes the light source 130, the interferometer 140, and the photodetector 150. The interferometer 140 is operably associated with the sample probe 200 in the catheter 190 by the sample path 142. The photodetectors 150a and 150b are operably associated with the digitizer 160 in the control room 110 by way of the digitizer paths 164. The digitizer 160 is operable with multiple inputs for the digitizer paths 164, as to accept multiple photodetectors 150 from multiple PIMs 180 and patient areas 120a and 120b. The CPU 170 in the control room 110 is for the imaging and processing of the images obtained from the catheter 190 and sample probe 200.

Figure 4D:
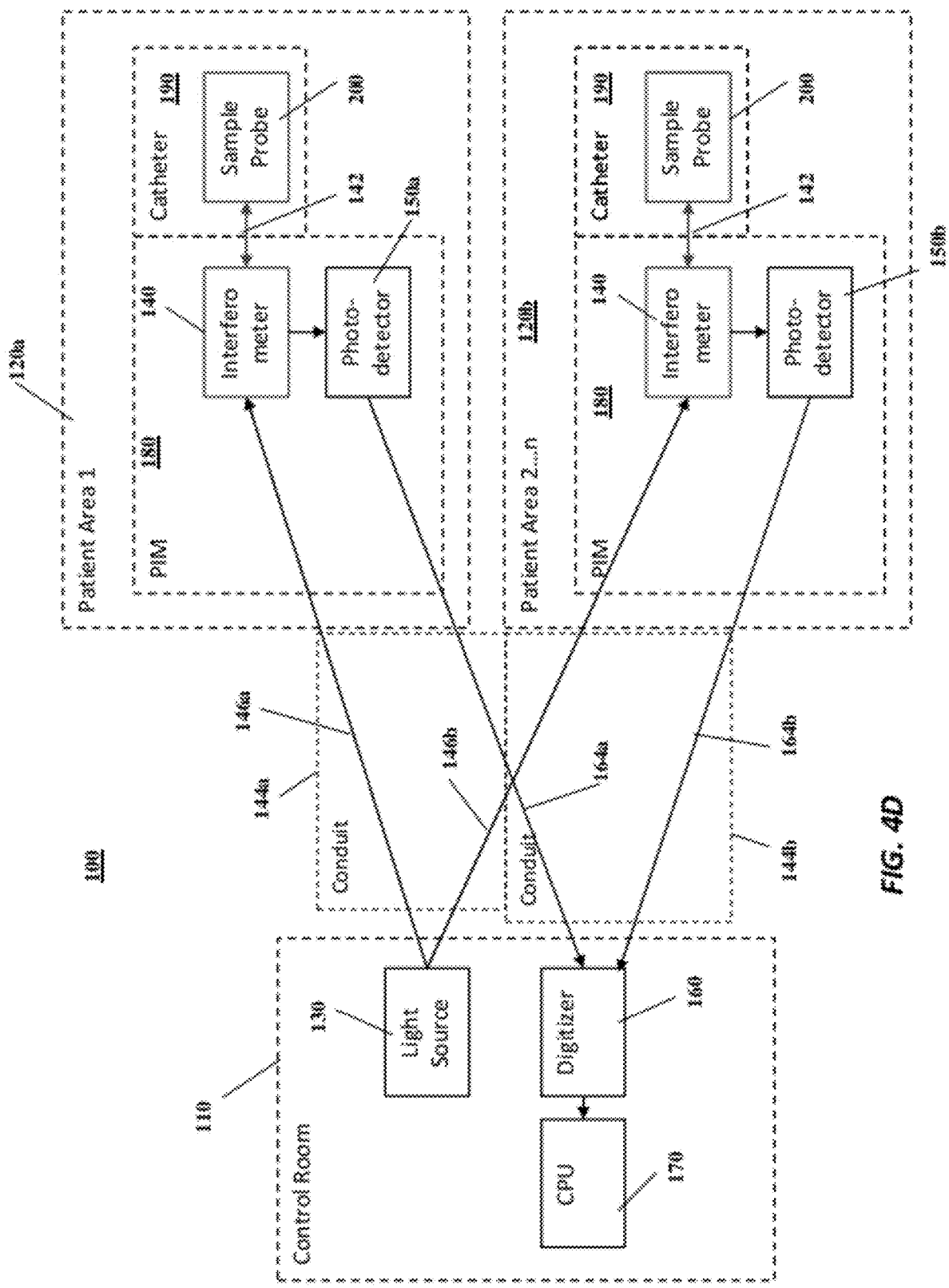
FIG. 4D is a schematic diagram of another distributed interferometer system.

In another embodiment, the integrated OCT system 100 is shown in FIG. 4D, which is another distributed interferometer system. The integrated OCT system 100 in this embodiment comprises the control room 110 including the light source 130, the digitizer 160, and the CPU 170, whereby the light source 130 is operably associated with at least two patient areas 120a and 120b. The patient areas 120a and 120b effectively distribute the light source's 130 capabilities to multiple patient areas when the control room 110 is located at a substantial physical distance away from such patient areas 120a and 120b. The patient areas 120a and 120b include the PIM 180 and the catheter 190, whereby the PIM 180 includes the interferometer 140 and the photodetector 150. The light source 130 is operably associated with the interferometers 140 in the PIMs 180 by the light paths 146a and 146b through the conduits 144a and 144b. The interferometers 140 are operably associated with the sample probe 200 in the catheter 190 by the sample path 142. The photodetectors 150a and 150b are operably associated with the digitizer 160 in the control room 110 by way of the digitizer paths 164a and 164b. The digitizer 160 is operable with multiple inputs for the digitizer paths 164a and 164b, as to accept multiple photodetectors 150 from multiple PIMs 180 and patient areas 120a and 120b. The digitizer 160 is operably associated with the CPU 170 in the control room 110 for imaging and processing.

Figure 4E:
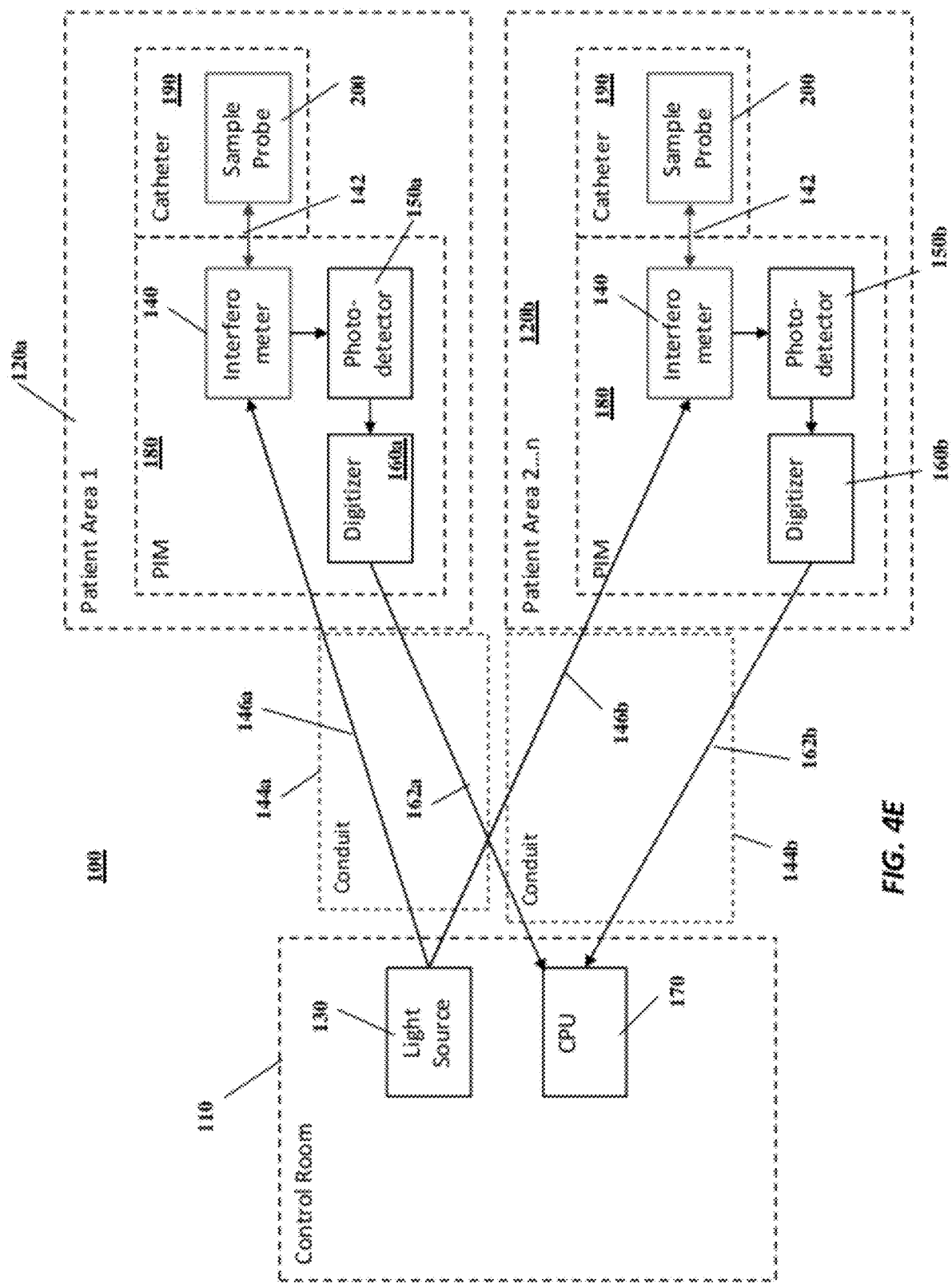
FIG. 4E is a schematic diagram of another distributed interferometer system.

In another embodiment, the integrated OCT system 100 is shown in FIG. 4E, which is another distributed interferometer system. The integrated OCT system 100 in this embodiment comprises the control room 110 including the light source 130 and the CPU 170, whereby the light source 130 is operably associated with at least two patient areas 120a and 120b. The patient areas 120a and 120b effectively distribute the light source's 130 capabilities to multiple patient areas when the control room 110 is located at a substantial physical distance away from such patient areas 120a and 120b. The patient areas 120a and 120b include the PIM 180 and the catheter 190, whereby the PIM 180 includes the interferometer 140, the photodetector 150, and the digitizers 160a and 160b. The light source 130 is operably associated with the interferometers 140 in the PIMs 180 by the light paths 146a and 146b through the conduits 144a and 144b. The interferometers 140 are operably associated with the sample probe 200 in the catheter 190 by the sample path 142. The photodetectors 150a and 150b are operably associated with the digitizers 160a and 160b in the PIM 180. The digitizers 160a and 160b are operable with the CPU 170 in the control room 110 by CPU paths 162a and 162b. The CPU 170 includes multiple inputs for the CPU paths 162a and 162b, as to accept multiple digitizers 160a and 160b from multiple PIMs 180 and patient areas 120a and 120b. The CPU 170 in the control room 110 is for the imaging and processing of the images obtained from the catheter 190 and sample probe 200.

Figure 4F:
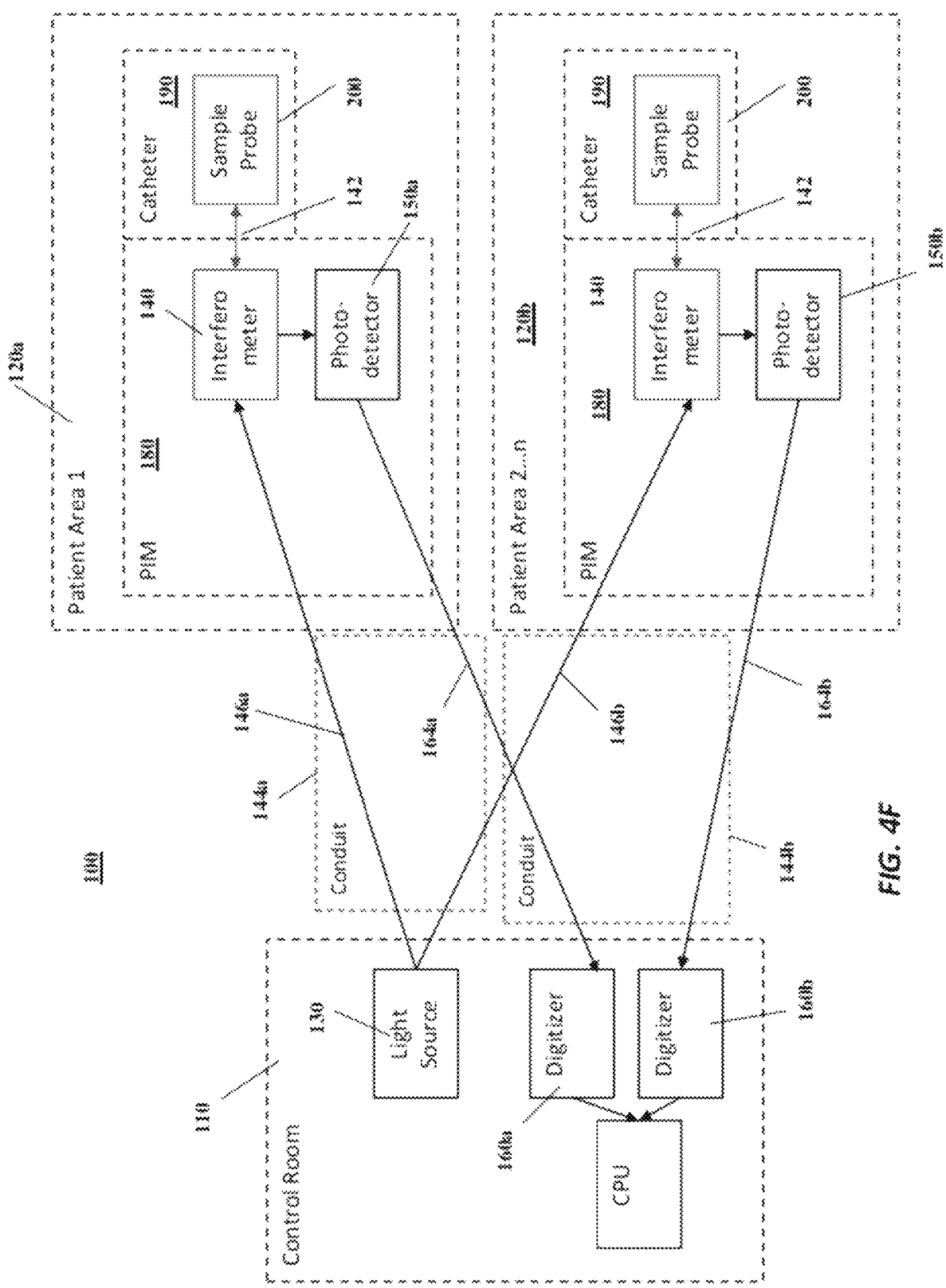
FIG. 4F is a schematic diagram of another distributed interferometer system.

In another embodiment, the integrated OCT system 100 is shown in FIG. 4F, which is another distributed interferometer system. The integrated OCT system 100 in this embodiment comprises the control room 110 including the light source 130, the digitizers 160a and 160b, and the CPU 170, whereby the light source 130 is operably associated with at least two patient areas 120a and 120b. The patient areas 120a and 120b effectively distribute the light source's 130 capabilities to multiple patient areas when the control room 110 is located at a substantial physical distance away from such patient areas 120a and 120b. The patient areas 120a and 120b include the PIM 180 and the catheter 190, whereby the PIM 180 includes the interferometer 140 and the photodetectors 150a and 150b. The light source 130 is operably associated with the interferometers 140 in the PIMs 180 by the light paths 146a and 146b through the conduits 144a and 144b. The interferometers 140 are operably associated with the sample probe 200 in the catheter 190 by the sample path 142. The photodetectors 150a and 150b are operably associated with the interferometer 140 and with the digitizers 160a and 160b in the control room 110 by way of the digitizer paths 164a and 164b from multiple PIMs 180 and patient areas 120a and 120b. The digitizers 160a and 160b are operably associated with the CPU 170 in the control room 110, such that the CPU 170 is able to accept multiple digitizers 160a and 160b. The CPU 170 in the control room 110 processes the images from multiple patient areas.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An integrated system comprising:
    a catheter configured to be disposed within a patient positioned on a bed;
    a rotating intravascular imaging probe configured to fit within the catheter, wherein the intravascular imaging probe is configured to be disposed within the patient; and
    an interface module comprising:
        a housing configured to be positioned on the bed;
        a motor that drives rotation of the intravascular imaging probe; and
        a digitizer configured to digitize and compress image data, wherein the motor and the digitizer are disposed within the housing of the interface module, wherein the rotating intravascular imaging probe is directly connected to the interface module; and
    a mobile console that is remote from the bed, the mobile console comprising:
        at least one mobile transport device;
        a central processing unit (CPU) component configured to receive and decompress the digitized image data from the interface module; and
        a display; and a connector cable extending between the mobile console and the interface module, wherein the interface module comprises a light source, a photodetector, and a spectrometer or an interferometer including a sample path and a reference path.

2. The integrated system of claim 1, wherein the mobile console comprises a laptop.

3. The integrated system according to claim 1, wherein the interface module further comprises a second motor that drives translation of the intravascular imaging probe.

4. The integrated system according to claim 1, wherein the interface module comprises the interferometer, wherein the interferometer comprises a variable delay line operably associated with either the sample path or the reference path.

5. The integrated system according to claim 1, wherein the interface module comprises the interferometer, wherein the interferometer comprises a sample clock generator.

6. The integrated system according to claim 1, wherein the interface module comprises the interferometer, wherein the interferometer is a fiber-based interferometer.

7. The integrated system according to claim 1, wherein the mobile console is remote from the interface module.

8. The integrated system according to claim 1, wherein the interface module comprises the interferometer, wherein the interferometer includes one or more fiber splitters or couplers for each of the sample path and the reference path.

9. The integrated system according to claim 1, wherein the interface module comprises the interferometer, wherein the sample path directly connects the interferometer to the catheter.

10. The integrated system according to claim 1, wherein the interface module comprises the interferometer, wherein the digitizer is connected to the interferometer through the photodetector.

11. The integrated system according to claim 1, wherein the CPU component is directly connected to the connector cable, and wherein the connector cable is directly connected to the interface module.

12. The integrated system according to claim 1, wherein the digitizer is configured to sample and convert continuous analog image signals into the digitized image data.

* * * * *